(12) United States Patent
Bandopadhayay et al.

(10) Patent No.: US 11,547,614 B2
(45) Date of Patent: Jan. 10, 2023

(54) METHODS AND COMPOSITIONS FOR STUDYING CELL EVOLUTION

(71) Applicants: THE BROAD INSTITUTE, INC., Cambridge, MA (US); DANA-FARBER CANCER INSTITUTE, INC., Boston, MA (US); MASSACHUSETTS INSTITUTE OF TECHNOLOGY, Cambridge, MA (US)

(72) Inventors: Pratiti Bandopadhayay, Boston, MA (US); Rameen Beroukhim, Boston, MA (US); Paul Blainey, Cambridge, MA (US); David Feldman, Cambridge, MA (US); Cory Johannessen, Cambridge, MA (US); Funien Tsai, Cambridge, MA (US)

(73) Assignees: THE BROAD INSTITUTE, INC., Cambridge, MA (US); DANA-FARBER CANCER INSTITUTE, INC., Boston, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 24 days.

(21) Appl. No.: 16/760,906

(22) PCT Filed: Oct. 31, 2018

(86) PCT No.: PCT/US2018/058519
§ 371 (c)(1),
(2) Date: Apr. 30, 2020

(87) PCT Pub. No.: WO2019/089803
PCT Pub. Date: May 9, 2019

(65) Prior Publication Data
US 2021/0180058 A1 Jun. 17, 2021

Related U.S. Application Data

(60) Provisional application No. 62/579,858, filed on Oct. 31, 2017.

(51) Int. Cl.
C12N 15/10 (2006.01)
C12N 15/113 (2010.01)
A61F 13/551 (2006.01)
A41D 19/00 (2006.01)

(52) U.S. Cl.
CPC ........ *A61F 13/5515* (2013.01); *A41D 19/002* (2013.01); *A41D 19/0075* (2013.01); *A61F 13/5518* (2013.01); *C12N 15/1079* (2013.01); *C12N 15/1082* (2013.01); *C12N 15/113* (2013.01); *A41D 19/0062* (2013.01); *A41D 2400/52* (2013.01); *A61F 2013/55155* (2013.01); *C12N 2310/20* (2017.05); *C12N 2320/10* (2013.01)

(58) Field of Classification Search
CPC .... C12N 9/22; C12N 15/113; C12N 15/1079; C12N 15/1082; C12N 2310/10; C12N 2310/20
USPC ..... 435/6.1, 9.1, 91.31, 455, 458; 514/44 A, 514/44 R; 536/23.1, 24.5
See application file for complete search history.

(56) References Cited

U.S. PATENT DOCUMENTS

| 4,873,316 | A | 10/1989 | Meade et al. |
| 5,543,158 | A | 8/1996 | Gref et al. |
| 5,580,859 | A | 12/1996 | Felgner et al. |
| 5,589,466 | A | 12/1996 | Felgner et al. |
| 5,593,972 | A | 1/1997 | Weiner et al. |
| 5,846,946 | A | 12/1998 | Huebner et al. |
| 5,855,913 | A | 1/1999 | Hanes et al. |
| 5,985,309 | A | 11/1999 | Edwards et al. |
| 6,007,845 | A | 12/1999 | Domb et al. |
| 6,603,061 | B1 | 8/2003 | Armstrong et al. |
| 6,750,059 | B1 | 6/2004 | Blakesley et al. |
| 7,259,015 | B2 | 8/2007 | Kingsman et al. |
| 7,303,910 | B2 | 12/2007 | Bebbington et al. |
| 7,351,585 | B2 | 4/2008 | Mitrophanous et al. |
| 7,745,651 | B2 | 6/2010 | Heyes et al. |
| 7,776,321 | B2 | 8/2010 | Cascalho et al. |
| 7,799,565 | B2 | 9/2010 | Maclachlan et al. |

(Continued)

FOREIGN PATENT DOCUMENTS

| EP | 0264166 A1 | 4/1988 |
| EP | 1519714 A1 | 4/2005 |

(Continued)

OTHER PUBLICATIONS

Mali et al (Science, vol. 339, No. 6121, pp. 823-826 (2013)), (Year: 2013).*

(Continued)

*Primary Examiner* — Jane J Zara
(74) *Attorney, Agent, or Firm* — F. Brent Nix, Esq.; Johnson, Marcou, Isaacs & Nix, LLC

(57) ABSTRACT

The subject matter disclosed herein is generally directed to methods and compositions for tagging cells of interest, tracking evolution of the tagged cells, and recovering the original tagged cells for further study. Specifically, cells are tagged with a DNA construct encoding a barcode sequence comprising a guide sequence. Barcoded cells can then be recovered using a reporter construct having CRISPR target sequences specific for the cell having a barcode of interest.

9 Claims, 32 Drawing Sheets
Specification includes a Sequence Listing.

(56) References Cited

U.S. PATENT DOCUMENTS

| | | |
|---|---|---|
| 7,803,397 B2 | 9/2010 | Heyes et al. |
| 7,838,658 B2 | 11/2010 | Maclachlan et al. |
| 7,868,149 B2 | 1/2011 | Boukharov et al. |
| 7,901,708 B2 | 3/2011 | Maclachlan et al. |
| 7,915,399 B2 | 3/2011 | Maclachlan et al. |
| 7,982,027 B2 | 7/2011 | Maclachlan et al. |
| 8,058,069 B2 | 11/2011 | Yaworski et al. |
| 8,101,741 B2 | 1/2012 | Maclachlan et al. |
| 8,188,263 B2 | 5/2012 | Maclachlan et al. |
| 8,236,943 B2 | 8/2012 | Lee et al. |
| 8,283,333 B2 | 10/2012 | Yaworski et al. |
| 8,404,658 B2 | 3/2013 | Hajjar et al. |
| 8,454,972 B2 | 6/2013 | Nabel et al. |
| 8,697,359 B1 | 4/2014 | Zhang |
| 8,709,843 B2 | 4/2014 | Shakuda |
| 8,771,945 B1 | 7/2014 | Zhang |
| 8,795,965 B2 | 8/2014 | Zhang |
| 8,865,406 B2 | 10/2014 | Zhang |
| 8,871,445 B2 | 10/2014 | Cong et al. |
| 8,889,356 B2 | 11/2014 | Zhang |
| 8,889,418 B2 | 11/2014 | Zhang |
| 8,895,308 B1 | 11/2014 | Zhang |
| 8,906,616 B2 | 12/2014 | Zhang |
| 8,932,814 B2 | 1/2015 | Cong et al. |
| 8,945,839 B2 | 2/2015 | Zhang |
| 8,993,233 B2 | 3/2015 | Zhang |
| 8,999,641 B2 | 4/2015 | Zhang |
| 2004/0013648 A1 | 1/2004 | Kingsman et al. |
| 2004/0171156 A1 | 9/2004 | Hartley et al. |
| 2004/0242517 A1 | 12/2004 | Cascalho |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0100536 A1 | 4/2009 | Adams et al. |
| 2009/0111106 A1 | 4/2009 | Mitrophanous et al. |
| 2010/0317109 A1 | 12/2010 | Maden et al. |
| 2011/0027239 A1 | 2/2011 | Paek |
| 2011/0059502 A1 | 3/2011 | Chalasani |
| 2011/0117189 A1 | 5/2011 | Mazzone et al. |
| 2011/0293571 A1 | 12/2011 | Widdowson et al. |
| 2011/0293703 A1 | 12/2011 | Mahon et al. |
| 2012/0251560 A1 | 10/2012 | Dahlman et al. |
| 2012/0251618 A1 | 10/2012 | Schrum et al. |
| 2012/0295960 A1 | 11/2012 | Palfi et al. |
| 2013/0244279 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang |
| 2014/0186958 A1 | 7/2014 | Zhang |
| 2014/0189896 A1 | 7/2014 | Zhang |
| 2014/0227787 A1 | 8/2014 | Zhang |
| 2014/0234972 A1 | 8/2014 | Zhang |
| 2014/0242664 A1 | 8/2014 | Zhang |
| 2014/0242699 A1 | 8/2014 | Zhang |
| 2014/0242700 A1 | 8/2014 | Zhang |
| 2014/0248702 A1 | 9/2014 | Zhang |
| 2014/0256046 A1 | 9/2014 | Zhang |
| 2014/0273231 A1 | 9/2014 | Zhang |
| 2014/0273232 A1 | 9/2014 | Zhang |
| 2014/0273234 A1 | 9/2014 | Zhang |
| 2014/0287938 A1 | 9/2014 | Zhang |
| 2014/0310830 A1 | 10/2014 | Zhang |
| 2014/0356959 A1* | 12/2014 | Church ............... C12N 15/11 435/468 |
| 2018/0057810 A1 | 3/2018 | Zhang |
| 2018/0127745 A1 | 5/2018 | Konermann |

FOREIGN PATENT DOCUMENTS

| | | | |
|---|---|---|---|
| EP | 1664316 A1 | 6/2006 | |
| EP | 1766035 A1 | 3/2007 | |
| EP | 1781593 A2 | 5/2007 | |
| EP | 2771468 A1 | 9/2014 | |
| EP | 2784162 A1 | 10/2014 | |
| EP | 2784162 B1 | 4/2015 | |
| EP | 2764103 B1 | 8/2015 | |
| WO | 9639154 A1 | 12/1996 | |
| WO | 9703211 A1 | 1/1997 | |
| WO | 2011028929 A3 | 10/2011 | |
| WO | 2012118717 A2 | 9/2012 | |
| WO | 2012135025 A2 | 10/2012 | |
| WO | 2014018423 A2 | 1/2014 | |
| WO | 2014047561 A1 | 3/2014 | |
| WO | 2014093595 A1 | 6/2014 | |
| WO | 2014093622 A2 | 6/2014 | |
| WO | 2014093635 A1 | 6/2014 | |
| WO | 2014093655 A2 | 6/2014 | |
| WO | 2014093661 A2 | 6/2014 | |
| WO | 2014093694 A1 | 6/2014 | |
| WO | 2014093701 A1 | 6/2014 | |
| WO | 2014093709 A1 | 6/2014 | |
| WO | 2014093712 A1 | 6/2014 | |
| WO | 2014093718 A1 | 6/2014 | |
| WO | 2014204723 A1 | 12/2014 | |
| WO | 2014204724 A1 | 12/2014 | |
| WO | 2014204725 A1 | 12/2014 | |
| WO | 2014204726 A1 | 12/2014 | |
| WO | 2014204727 A1 | 12/2014 | |
| WO | 2014204728 A1 | 12/2014 | |
| WO | 2014204729 A1 | 12/2014 | |
| WO | 2015006294 A2 | 1/2015 | |
| WO | WO-2015006294 A2 * | 1/2015 | ............... C07K 2/00 |
| WO | 2015065964 A1 | 5/2015 | |
| WO | 2016040476 A1 | 3/2016 | |
| WO | 2016070037 A2 | 5/2016 | |
| WO | WO-2016070037 A2 * | 5/2016 | ......... A61K 31/4709 |
| WO | 2016205745 A2 | 12/2016 | |
| WO | 2018005691 A1 | 1/2018 | |

OTHER PUBLICATIONS

Abudayyeh, et al., "C2c2 is a single-component programmable RNA-guided RNA-targeting CRISPR effector", Science, vol. 353, Issue 6299, Aug. 15, 2016, 65 pages.
Sorek, et al., "CRISPR-Mediated Adaptive Immune Systems in Bacteria and Archaea", Annual Review of Biochemistry, vol. 82, Mar. 11, 2013, pp. 237-266.
International Search Report and Written Opinion dated Jan. 17, 2017 by the U.S. Patent Office for PCT/US2018/058519.
Ahmad, et al., "In Silico Modelling of Drug-Polymer Interactions for Pharmaceutical Formulations", Journal of the Royal Society Interface, vol. 7, Issue Suppl_4, Jun. 2, 2010, S423-S433.
Akinc, et al., "A Combinatorial Library of Lipid-like Materials for Delivery of RNAi Therapeutics", Nature Biotechnology, vol. 26, Issue 5, May 2008, 561-569.
Alabi, et al., "Multiparametric Approach for the Evaluation of Lipid Nanoparticles for siRNA Delivery", Proceedings of the National Academy of Sciences, vol. 110, No. 32, Jul. 23, 2013, 12881-12886.
Alhasan, et al., "Exosome Encased Spherical Nucleic Acid Gold Nanoparticle Conjugates as Potent MicroRNA Regulation Agents", Small, vol. 10, Issue 1, Jan. 15, 2014, 186-192.
Altschul, et al., "Basic Local Alignment Search Tool", Journal of Molecular Biology, vol. 215, No. 3, Oct. 5, 1990, 403-410.
Alvarez-Erviti, et al., "Delivery of siRNA to the Mouse Brain by Systemic Injection of Targeted Exosomes", Nature Biotechnology, vol. 29, No. 4, Apr. 2011, 341-345.
Amann, et al., "Tightly Regulated Tac Promoter Vectors Useful for the Expression of Unfused and Fused Proteins in *Escherichia coli*", Gene, vol. 69, Issue 2, Sep. 30, 1988, 301-315.
Ausubel, "A Botanical Macroscope", Proceedings of National Academy of Sciences, vol. 106, No. 31, Aug. 4, 2009, 12569-12570.

(56) References Cited

OTHER PUBLICATIONS

Balagaan, et al., "Stable and Efficient Intraocular Gene Transfer Using Pseudotyped EIAV Lentiviral Vectors", The Journal of Gene Medicine, vol. 8, Issue 3, Mar. 2006, 275-285.

Baldari, "A Novel Leader Peptide which Allows Efficient Secretion of a Fragment of Human Interleukin 13 in *Saccharomyces cerevisiae*", The EMBO Journal, vol. 6, No. 1, 1987, 229-234.

Banerji, et al., "A Lymphocyte-Specific Cellular Enhancer is Located Downstream of the Joining Region in Immunoglobulin Heavy Chain Genes", Cell, vol. 33, Issue 3, Jul. 1983, 729-740.

Barros, et al., "Safety Profile of RNAi Nanomedicines", Advanced Drug Delivery Reviews, vol. 64, Issue 15, Dec. 2012, 1730-1737.

Bartlett, et al., "Impact of Tumor-Specific Targeting on The Biodistribution and Efficacy of Sirna Nanoparticles Measured by Multimodality In Vivo Imaging", Proceedings of the National Academy of Sciences, vol. 104, No. 39, Sep. 25, 2007, 15549-15554.

Basha, et al., "Influence of Cationic Lipid Composition on Gene Silencing Properties of Lipid Nanoparticle Formulations of siRNA in Antigen-Presenting Cells", Molecular Therapy, vol. 19, No. 12, Dec. 2011, 2186-2200.

Binley, et al., "Safety and Biodistribution of an Equine Infectious Anemai Virus-Based Gene Therapy, RetinoStat, for Age-Related Macular Degeneration", Human Gene Therapy, vol. 23, Sep. 2012, 980-991.

Birrel, "A Genome-Wide Screen in *Saccharomyces cerevisiae* for Genes Affecting UV Radiation Sensitivity", PNAS, vol. 98, No. 22, Oct. 23, 2001, 12608-12613.

Boshart, et al., "A Very Strong Enhancer is Located Upstream of an Immediate Early Gene of Human Cytomegalovirus", Cell, vol. 41, No. 2, Jun. 1985, 521-530.

Brooks, et al., "Efficient Gene Editing in Tomato in the First Generation Using the Clustered Regularly Interspaced Short Palindromic Repeats/CRISPR-Associated9 System", Plant Physiology, vol. 166, No. 3, Nov. 2014, 1292-1297.

Buskirk, et al., "Directed Evolution of Ligand Dependence: Small-Molecule-Activated Protein Splicing", Proceedings of the National Academy of Sciences, vol. 101, No. 29, Jul. 20, 2004, 10505-10510.

Byrne, et al., "Multiplex Gene Regulation: A Two-Tiered Approach to Transgene Regulation in Transgenic Mice", Proceedings of the National Academy of Sciences, vol. 86, Jul. 1989, 5473-5477.

Calame, et al., "Transcriptional Controlling Elements in the Immunoglobulin and T Cell Receptor Loci", Advances in Immunology, vol. 43 (Abstract only), Feb. 1988, 235-275.

Caliando, et al., "Targeted DNA Degradation using a CRISPR Device Stably Carried in the Host Genome", Nature Communications, vol. 6, No. 6989, May 19, 2015, 10 pages.

Camper, et al., "Postnatal Repression of the Alpha-Fetoprotein Gene is Enhancer Independent", Genes and Development, vol. 3, 1989, 537-546.

Carr, et al., "Genome Engineering", Nature Biotechnology, vol. 27, No. 12, Dec. 9, 2009, 1151-1162.

Cbol Plant Working Group, "A DNA Barcode for Land Plants", Proceedings of National Academy of Sciences, vol. 106, No. 31, Aug. 4, 2009, 12794-12797.

Chen, et al., "Genome-Wide CRISPR Screen in a Mouse Model of Tumor Growth and Metastasis", Cell, vol. 160, No. 6, Mar. 12, 2015, 28 pages.

Chen, et al., "Predicting Peptide-Mediated Interactions on a Genome-Wide Scale", PLOS Computational Biology, vol. 11, No. 5, May 4, 2015, 13 pages.

Cho, et al., "Lipid-like Nanoparticles for Small Interfering RNA Delivery to Endothelial Cells", Advanced Functional Materials, vol. 19, Issue 19, Oct. 9, 2009, 3112-3118.

Choi, et al., "Mechanism for the Endocytosis of Spherical Nucleic Acid Nanoparticle Conjugates", Proceedings of the National Academy of Sciences, vol. 110, No. 19, 2013, 7625-7630.

Coelho, et al., "Safety and Efficacy of RNAi Therapy for Transthyretin Amyloidosis", The New England Journal of Medicine, vol. 369, Issue 9, Aug. 29, 2013, 819-829.

Cong, et al., "Multiplex Genome Engineering Using CRISPR/Cas Systems", Science, vol. 339, No. 6121, Feb. 15, 2013, 819-823.

Cronican, et al., "A Class of Human Proteins That Deliver Functional Proteins Into Mammalian Cells In Vitro and In Vivo", Chemistry & Biology, vol. 18, Issue 7, Jul. 29, 2011, 833-838.

Cronican, et al., "Potent Delivery of Functional Proteins into Mammalian Cells in Vitro and in Vivo Using a Supercharged Protein", ACS Chemical Biology, vol. 5, No. 8, 2010, 747-752.

Cutler, et al., "Polyvalent Nucleic Acid Nanostructures", Journal of the American Chemical Society, vol. 133, Issue 24, Jun. 22, 2011, 9254-9257.

Cutler, et al., "Spherical Nucleic Acids", Journal of the American Chemical Society, vol. 134, Issue 3, 2012, 1376-1391.

Dahlman, et al., "In Vivo Endothelial siRNA Delivery Using Polymeric Nanoparticles wiht Low Molecular Weight", Nature Nanotechnology, vol. 9, No. 8, Aug. 2014, 648-655.

Davis, et al., "Evidence of RNAi in Humans From Systemically Administered siRNA via Targeted Nanoparticles", Nature, vol. 464, No. 7291, Apr. 15, 2010, 1067-1070.

Davis, et al., "Small Molecule-Triggered Cas9 Protein with Improved Genome-Editing Specificity", Nature Chemical Biology, vol. 11, No. 5, May 2015, 316-318.

Devereux, et al., "A Comprehensive Set of Sequence Analysis Programs for the VAX", Nucleic Acids Research, vol. 12, No. 1, Jan. 11, 1984, 387-395.

Dey, et al., "Toward a "Structural BLAST": Using Structural Relationships to Infer Function", Protein Science, vol. 22, No. 4, Apr. 2013, 359-366.

Digiusto, et al., "RNA-Based Gene Therapy for HIV with Lentiviral Vector-Modified CD34(+) Cells in Patients Undergoing Transplantation for AIDSrelated Lymphoma", Science Translational Medicine, vol. 2, Issue 36, Jun. 16, 2010, 8 pages.

Dirk, et al., "Toward Whole-Transcriptome Editing with CRISPR-Cas9", Molecular Cell, vol. 58, No. 4, May 21, 2015, 560-562.

Doench, et al., "Rational Design of Highly Active SgRNAs for CRISPR-Cas9-Mediated Gene Inactivation", Nature Biotechnology, vol. 32, No. 12, Dec. 2014, 17 pages.

Edlund, et al., "Cell-Specific Expression of the Rat Insulin Gene: Evidence for Role of Two Distinct 5' Flanking Elements", Science. vol. 230, No. 4728, Nov. 22, 1985, 912-916.

El-Andaloussi, et al., "Exosome-Mediated Delivery of siRNA in Vitro and in Vivo", Nature Protocols, vol. 7, Issue 12, Dec. 2012, 2112-2126.

Feng, et al., "Efficient Genome Editing in Plants using a CRISPR/Cas System", Cell Research, vol. 23, Issue 10, Oct. 2013, 1229-1232.

Fu, et al., "High Frequency Off-Target Mutagenesis Induced by CRISPR-Cas Nucleases in Human Cells", Nature Biotechnology, vol. 31, No. 9, Sep. 2013, 822-826.

Fu, et al., "Improving CRISPR-Cas Nuclease Specificity Using Truncated Guide RNAS", Nature Biotechnology, vol. 32, No. 3, Mar. 2014, 18 pages.

Garrett, et al., "Exploring Uptake Mechanisms of Oral Nanomedicines using Multimodal Nonlinear Optical Microscopy", Journal of Biophotonics, vol. 5, Issue 5-6, May 2012, 458-468.

Garrett, et al., "Label-Free Imaging of Polymeric Nanomedicines using Coherent Anti-Stokes Raman Scattering Microscopy", Journal of Raman Spectroscopy, vol. 43, Issue 5, May 2012, 681-688.

Geisbert, et al., "Postexposure Protection of Non-Human Primates Against a Lethal Ebola Virus Challenge with RNA Interference: A Proof-of-Concept Study", The Lancet, vol. 375, Issue 9729, May 29-Jun. 4, 2010, 1896-1905.

Giaever, et al., "Functional Profiling of the *Saccharomyces cerevisiae* Genome", Nature, vol. 418, Jul. 25, 2002, 387-391.

Grimm, et al., "In Vitro and In Vivo Gene Therapy Vector Evolution via Multispecies Interbreeding and Retargeting of Adeno-Associated Viruses", Journal of Virology, vol. 82, No. 12, Jun. 2008, 5887-5911.

Groenen, et al., "Nature of DNA Polymorphism in the Direct Repeat Cluster of *Mycobacterium tuberculosis*; Application for Strain Differentiation by a Novel Typing Method", Molecular Microbiology, vol. 10, No. 5, Jan. 1994 , 10 pages.

(56) References Cited

OTHER PUBLICATIONS

Guilinger, et al., "Fusion of Catalytically Inactive Cas9 to FokI Nuclease Improves the Specificity of Genome Modification", Nature Biotechnology, vol. 32, No. 6, Jun. 2014, 577-582.
Hao, et al., "Nucleic Acid-Gold Nanoparticle Conjugates as Mimics of microRNA", Small, vol. 7, Issue 22, Nov. 18, 2011, 3158-3162.
Hoe, et al., "Rapid Molecular Genetic Subtyping of Serotype M1 Group a *Streptococcus* Strains", Emerging Infectious Diseases, vol. 5, No. 2, Mar.-Apr. 1999, 254-263.
Horwell, "The 'Peptoid' Approach to the Design of Non-Peptide, Small Molecule Agonists and Antagonists of Neuropeptides", Trends in Biotechnology, vol. 13, No. 4, Apr. 1, 1995, 132-134.
Hsu, et al., "Development and Applications of Crispr-Cas9 for Genome Engineering", Cell, vol. 157, No. 6, Jun. 5, 2014, 34 pages.
Hsu, et al., "DNA Targeting Specificity of RNA-Guided Cas9 Nucleases", Nature Biotechnology, vol. 31, No. 9, Sep. 2013, 827-832.
Hyo-Eun, et al., "Studying Clonal Dynamics in Response to Cancer Therapy Using High-Complexity Barcoding", Nature Medicine, vol. 21, No. 5, May 2015, 440-448.
Ishino, et al., "Nucleotide Sequence of the iap Gene, Responsible for Alkaline Phosphatase Isozyme Conversion in *Escherichia coli*, and Identification of the Gene Product", Journal of Bacteriology, vol. 169, No. 12, Dec. 1987, 5429-5433.
Jansen, et al., "Identification of a Novel Family of Sequence Repeats among Prokaryotes", OMICS: A Journal of Integrative Biology, vol. 6, No. 1, Feb. 2002, 23-33.
Jansen, et al., "Identification of Genes that are Associated with DNA Repeats in Prokaryotes", Molecular Microbiology, vol. 43, Issue 6, Apr. 25, 2002, 1565-1575.
Jayaraman, et al., "Maximizing the Potency of siRNA Lipid Nanoparticles for Hepatic Gene Silencing In Vivo", Angew. Chem. Int. Ed., vol. 51, 2012, 8529-8533.
Jensen, et al., "Spherical Nucleic Acid Nanoparticle Conjugates as an RNAi-Based Therapy for Glioblastoma", Science Translational Medicine, vol. 5, Issue 209, Oct. 30, 2013, 12 pages.
Jiang, et al., "Lipidoid-coated Iron Oxide Nanoparticles for Efficient DNA and siRNA Delivery", Nano Letters, vol. 13, No. 3, Mar. 13, 2013, 1059-1064.
Jiang, et al., "RNA-Guided Editing of Bacterial Genomes Using CRISPR-Cas Systems", Nature Biotechnology, vol. 31, No. 3, Mar. 2013, 9 pages.
Judge, et al., "Confirming the RNAi-Mediated Mechanism of Action of siRNA-Based Cancer Therapeutics in Mice", The Journal of Clinical Investigation, vol. 119, No. 3, Mar. 2009, 661-673.
Karagiannis, et al., "Rationally Designed Tumor-Penetrating Nanocomplexes", AC Nano, vol. 6, No. 10, 2012, 8484-8487.
Karginov, et al., "The CRISPR System: Small RNA-Guided Defense in Bacteria and Archaea", Molecular Cell, vol. 37, Issue 1, Jan. 15, 2010, 23 pages.
Kaufman, et al., "Translational Efficiency of Polycistronic MRNAs and their Utilization to Express Heterologous Genes in Mammalian Cells", The Embo Journal, vol. 6, No. 1, 1987, 187-195.
Kessel, et al., "Murine Developmental Control Genes", Science, vol. 249, No. 4967, Jul. 27, 1990, 374-379.
Klein, et al., "Droplet Barcoding for Single-Cell Transcriptomics Applied to Embryonic Stem Cells", Cell, vol. 161, No. 5, May 21, 2015, 24 pages.
Koch, "Combining Morphology and DNA Barcoding Resolves the Taxonomy of Western Malagasy Liotrigona Moure, 1961 (Hymenoptera: Apidae: Meliponini)", African Invertebrates, vol. 51, No. 2, Dec. 2010, 413-421.
Konermann, et al., "Genome-Scale Transcriptional Activation by an Engineered CRISPR-Cas9 Complex", Nature, vol. 517, No. 7536, Jan. 29, 2015, 583-588.
Konermann, et al., "Optical Control of Mammalian Endogenous Transcription and Epigenetic States", Nature, vol. 500, No. 7463, Aug. 22, 2013, 18 pages.
Kormann, et al., "Expression of Therapeutic Proteins after Delivery of Chemically Modified mRNA in Mice", Nature Biotechnology, vol. 29, 2011, 154-157.
Kress, et al., "DNA Barcodes: Genes, Genomics, and Bioinformatics", Proceedings of the National Academy of Sciences of the United States of America, vol. 105, No. 8, Feb. 26, 2008, 2761-2762.
Kress, et al., "Use of DNA Barcodes to Identify Flowering Plants", PNAS, vol. 102, No. 23, Jun. 7, 2005, 8369-8374.
Kuhar, et al., "Novel Fluorescent Genome Editing Reporters for Monitoring DNA Repair Pathway Utilization at Endonuclease-Induced Breaks", Nucleic Acids Research, vol. 42, No. 1, Oct. 2013, 11 pages.
Kurjan, et al., "Structure of a Yeast Pheromone Gene (Mfα): A Putative A-Factor Precursor Contains Four Tandem Copies of Mature A-Factor", Cell, vol. 30, No. 3, Nov. 1982, 933-943.
Lahaye, et al., "DNA Barcoding the Floras of Biodiversity Hotspots", Proceedings of the National Academy of Sciences, vol. 105, No. 8, Feb. 26, 2008, 2923-2928.
Lalatsa, et al., "A Prodrug Nanoparticle Approach for the Oral Delivery of a Hydrophilic Peptide, Leucine(5)-enkephalin, to the Brain", Molecular Pharmaceutics, vol. 9, No. 6, Jun. 4, 2012, 1665-1680.
Lalatsa, et al., "Amphiphilic Poly(L-amino acids)—New Materials for Drug Delivery", Journal of Controlled Release, vol. 161, No. 2, Jul. 20, 2012, 523-536.
Lalatsa, et al., "Delivery of Peptides to the Blood and Brain After Oral Uptake of Quaternary Ammonium Palmitoyl Glycol Chitosan Nanoparticles", Molecular Pharmaceutics, vol. 9, No. 6, Jun. 4, 2012, 1764-1774.
Lawrence, et al., "Supercharging Proteins Can Impart Unusual Resilience", Journal of the American Chemical Society, vol. 129, Issue 33, Aug. 1, 2007, 10110-10112.
Lee, et al., "Molecularly Self-Assembled Nucleic Acid Nanoparticles for Targeted in Vivo siRNA Delivery", Nature Nanotechnology, vol. 7, No. 6, Jan. 22, 2014, 389-393.
Lewis, et al., "Efficient Delivery of siRNA for Inhibition of Gene Expression in Postnatal Mice", Nature Genetics, vol. 32, Sep. 2002, 107-108.
Livingstone, et al., "Protein Sequence Alignments: a Strategy for the Hierarchical Analysis of Residue Conservation", Bioinformatics, vol. 9, Issue 6, Dec. 1, 1993, 745-756.
Luckow, et al., "High Level Expression of Nonfused Foreign Genes with Autographa Californica Nuclear Polyhedrosis Virus Expression Vectors", Virology, vol. 170, Issue 1, May 1989, 31-39.
Macosko, et al., "Highly Parallel Genome-Wide Expression Profiling of Individual Cells Using Nanoliter Droplets", Cell, vol. 161, No. 5, May 21, 2015, 25 pages.
Mali, et al., "Barcoding Cells Using Cell-Surface Programmable DNA-Binding Domains", Nature Methods, vol. 10, No. 5, May 2013, 403-406.
Mali, et al., "CAS9 Transcriptional Activators for Target Specificity Screening and Paired Nickases for Cooperative Genome Engineering", Nature Biotechnology, vol. 31, No. 9, Sep. 2013, 833-838.
Mali, et al., "RNA-Guided Human Genome Engineering via Cas9", Science, vol. 339, No. 6121, Feb. 15, 2013, 8 pages.
Mazza, et al., "Nanofiber-Based Delivery of Therapeutic Peptides to the Brain", ACS Nano, vol. 7, No. 2, Jan. 4, 2013, 1016-1026.
Mcnaughton, et al., "Mammalian Cell Penetration, siRNA Transfection, and DNA Transfection by Supercharged Proteins", PNAS, vol. 106, No. 15, Apr. 14, 2009, 6111-6116.
Mirkin, "Interview: An Interview with Chad Mirkin: Nanomedicine Expert", Nanomedicine, vol. 7, Issue 5, May 2012, 635-638.
Mojica, et al., "Long Stretches of Short Tandem Repeats are Present in the Largest Replicons of the Archaea Haloferax Mediterranei and Haloferax Volcanii and Could be Involved in Replicon Partitioning", Molecular Microbiology, vol. 17, No. 1, Jul. 1995, 85-93.
Mojica, et al., "MicroCorrespondence: Biological significance of a family of regularly spaced repeats in the genomes of Archaea, Bacteria and mitochondria", Molecular Microbiology, vol. 36, No. 1, Apr. 2000, 244-246.
Morrell, et al., "Crop Genomics: Advances and Applications", Nature Reviews Genetics, vol. 13, Feb. 2012, 85-96.

(56) References Cited

OTHER PUBLICATIONS

Morrissey, et al., "Potent and persistent in vivo anti-HBV activity of chemically modified siRNAs," Nature Biotechnology, vol. 23, No. 8, Aug. 2005.
Nakamura, et al., "Codon Usage Tabulated from International DNA Sequence Databases: Status for the Year 2000", Nucleic Acids Research, vol. 28, No. 1, 2000, p. 292.
Nakata, et al., "Unusual Nucleotide Arrangement with Repeated Sequences in the *Escherichia coli* K-12 Chromosome", Journal of Bacteriology, vol. 171, No. 6, Jun. 1989, 3553-3556.
Nishimasu, et al., "Crystal Structure of Cas9 in Complex with Guide RNA and Target DNA", Cell, vol. 156, No. 5, Feb. 27, 2014, 25 pages.
Nishimasu, et al., "Crystal Structure of *Staphylococcus aureus* Cas9", Cell, vol. 162, No. 5, Aug. 27, 2015, 24 pages.
Nolan-Stevaux, et al., "Measurement of Cancer Cell Growth Heterogeneity through Lentiviral Barcoding Identifies Clonal Dominance as a Characteristic of In Vivo Tumor Engraftment", PLOS ONE, vol. 8, Issue 6, Jun. 2013, 11 pages.
Novobrantseva, et al., "Systemic RNAi-mediated Gene Silencing in Nonhuman Primate and Rodent Myeloid Cells", Molecular Therapy—Nucleic Acids, 2012, 13 pages.
O'Hare, et al., "Transformation of Mouse Fibroblasts to Methotrexate Resistance by a Recombinant Plasmid Expressing a Prokaryotic Dihydrofolate Reductase", Proceedings of the National Academy of Sciences, vol. 78, No. 3, Mar. 1981, 1527-1531.
Parnas, et al., "A Genome-Wide CRISPR Screen in Primary Immune Cells to Dissect Regulatory Networks", Cell, vol. 162, No. 3, Jul. 30, 2015, 24 pages.
Peck, et al., "Directed Evolution of a Small Molecule-Triggered Intein with Improved Splicing Properties in Mammalian Cells", Cell Chemical Biology, vol. 18, No. 5, May 27, 2011, 619-630.
Perler, "InBase: the Intein Database", Nucleic Acids Research, vol. 30, No. 1, Jan. 1, 2002, 383-384.
Pinkert, et al., "An Albumin Enhancer Located 10 kb Upstream Functions Along with its Promoter to Direct Efficient, Liver-Specific Expression in Transgenic Mice", Genes and Development, vol. 1, No. 3, May 1987, 268-277.
Platt, et al., "CRISPR-Cas9 Knockin Mice for Genome Editing and Cancer Modeling", Cell, vol. 159, No. 2, Oct. 9, 2014, 31 pages.
Porter, et al., "Lentiviral and Targeted Cellular Barcoding Reveals Ongoing Clonal Dynamics of Cell Lines In Vitro and In Vivo", Genome Biology, vol. 15, No. 5, 2014, 14 pages.
Qu, et al., "Carbohydrate-Based Micelle Clusters which Enhance Hydrophobic Drug Bioavailability by up to 1 Order of Magnitude", Biomacromolecules, vol. 7, Issue 12, Dec. 2006, 3452-3459.
Queen, et al., "Immunoglobulin Gene Transcription is Activated by Downstream Elements", Cell, vol. 33, No. 3, Aug. 1983, 741-748.
Ramakrishna, et al., "Surrogate Reporter-Based Enrichment of Cells Containing RNA-Guided Cas9 Nuclease-Induced Mutations", Nature Communications, vol. 5, No. 3378, Feb. 2014.
Ramanan, et al., "CRISPR/Cas9 Cleavage of Viral DNA Efficiently Suppresses Hepatitis B Virus", Scientific Reports, vol. 5, Article No. 10833, Jun. 2, 2015, 9 pages.
Ran, et al., "Double Nicking by RNA-Guided CRISPR Cas9 for Enhanced Genome Editing Specificity", Cell, vol. 154, No. 6, Sep. 12, 2013, 19 pages.
Ran, et al., "Genome Engineering Using the CRISPR-Cas9 System", Nature Protocols, vol. 8, No. 11, Nov. 2013, 49 pages.
Ran, et al., "In Vivo Genome Editing using *Staphylococcus aureus* Cas9", Nature, vol. 520, No. 7546, Apr. 1, 2015, 30 pages.
Reich, et al., "Small Interfering RNA (siRNA) Targeting VEGF Effectively Inhibits Ocular Neovascularization in a Mouse Model", Molecular Vision, vol. 9, May 2003, 210-216.
Ren, et al., "Light Activation of Protein Splicing with a Photocaged Fast Intein", Journal of the American Chemical Society, vol. 137, No. 6, 2015, 2155-2158.
Schiffelers, et al., "Cancer siRNA Therapy by Tumor Selective Delivery with Ligand-Targeted Sterically Stabilized Nanoparticle", Nucleic Acids Research, vol. 32, No. 19, e149, 2004, 10 pages.

Schroeder, et al., "Lipid-Based Nanotherapeutics for siRNA Delivery", Journal of Internal Medicine, vol. 267, No. 1, Jan. 2010, 9-21.
Schultz, "Expression and Secretion in Yeast of a 400-Kda Envelope Glycoprotein Derived from Epstein-Barr Virus", Gene, vol. 54, No. 1, 1987, 113-123.
Seberg, et al., "How Many Loci Does it Take to DNA Barcode a Crocus?", Public Library of Sciences, vol. 4, No. 2, Feb. 25, 2009, 6 pages.
Semple, et al., "Rational Design of Cationic Lipids for siRNA Delivery", Nature Biotechnology, vol. 28, Issue 2, Jan. 17, 2010, 172-177.
Seroz, "International Preliminary Report on Patentability issued in International Application No. PCT/US2016/038234", dated Dec. 28, 2017, 12 pages.
Seroz, "International Search Report and Written Opinion issued in International Application No. PCT/US2016/038234", dated Apr. 24, 2017, 19 pages.
Shalem, et al., "Genome-Scale CRISPR-Cas9 Knockout Screening in Human Cells", Science, vol. 343, No. 6166, Jan. 3, 2014, 84-87.
Shalem, et al., "High-Throughput Functional Genomics Using CRISPR-Cas9", Nature Reviews Genetics, vol. 16, No. 5, May 2015, 28 pages.
Shan, et al., "Targeted Genome Modification of Crop Plants Using a CRISPR-Cas System", Nature biotechnology, vol. 31, No. 8, Aug. 2013, 686-688.
Shen, et al., "Gene Silencing by Adenovirus-Delivered siRNA", FEBS Letters, vol. 539, Mar. 2003, 111-114.
Shmakov, et al., "Discovery and Functional Characterization of Diverse Class 2 CRISPR-Cas Systems", Molecular Cell, vol. 60, No. 3, Nov. 5, 2015, 23 pages.
Siew, et al., "Enhanced Oral Absorption of Hydrophobic and Hydrophilic Drugs Using Quaternary Ammonium Palmitoyl Glycol Chitosan Nanoparticles", Molecular Pharmaceutics, vol. 9, Issue 1, Jan. 1, 2012, 14-28.
Simeoni, et al., "Insight into the Mechanism of the Peptide-Based Gene Delivery System MPG: Implications for Delivery of siRNA into Mammalian Cells", Nucleic Acids Research, vol. 31, No. 11, 2003, 2717-2724.
Simon, et al., "Peptoids: A Modular Approach to Drug Discovery", PNAS, vol. 89, No. 20, Oct. 1992, 9367-9371.
Smith, et al., "Production of Human Beta Interferon in Insect Cells Infected with a Baculovirus Expression Vector", Molecular and Cellular Biology, vol. 3, No. 12, Dec. 1983, 2156-2165.
Smith, et al., "Single-Step Purification of Polypeptides Expressed in *Escherichia coli* as Fusions With Glutathione S-Transferase", Gene, vol. 67, No. 1, Jul. 15, 1988, 31-40.
Soininen, et al., "Analysing Diet of Small Herbivores: The Efficiency of DNA Barcoding Coupled with High-Throughput Pyrosequencing for Deciphering the Composition of Complex Plant Mixtures", Frontiers in Zoology, vol. 6, No. 1, Aug. 2009, 10 pages.
Sorensen, et al., "Gene Silencing by Systemic Delivery of Synthetic siRNAs in Adult Mice", Journal of Molecular Biology, vol. 327, Apr. 4, 2003, 761-766.
Spuch, et al., "Liposomes for Targeted Delivery of Active Agents against Neurodegenerative Diseases (Alzheimer's Disease and Parkinson's Disease)", Journal of Drug Delivery, vol. 2011, Article ID 469679, 2011, 12 pages.
Studier, et al., "Use of T7 RNA Polymerase to Direct Expression of Cloned Genes", Methods in Enzymology, vol. 185, 1990, 60-89.
Su, et al., "In Vitro and In Vivo mRNA Delivery Using Lipid-Enveloped pH-Responsive Polymer Nanoparticles", Molecular Pharmaceutics, vol. 8, No. 3, Jun. 6, 2011, 774-787.
Swiech, et al., "In Vivo Interrogation of Gene Function in the Mammalian Brain Using CRISPR-Cas9", Nature Biotechnology, vol. 33, No. 1, Jan. 2015, 9 pages.
Tabernero, et al., "First-in-Humans Trial of an RNA Interference Therapeutic Targeting VEGF and KSP in Cancer Patients with Liver Involvement", Cancer Discovery, vol. 3, No. 4, Apr. 2013, 406-417.
Takebe, et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, Jan. 1988, 466-472.

(56) References Cited

OTHER PUBLICATIONS

Tatusova, et al., "BLAST 2 Sequences, a New Tool for Comparing Protein and Nucleotide Sequences", FEMS Microbiology Letters, vol. 174, Issue 2, 1999, 247-250.
Tatusova, et al., "Erratum to "BLAST 2 Sequences, a New Tool for Comparing Protein and Nucleotide Sequences"", FEMS Microbiology Letters, vol. 177, Issue 1, 1999, 187-188.
Taylor, et al., "The Classification of Amino Acid Conservation", Journal of Theoretical Biology, vol. 119, No. 2, Mar. 21, 1986, 205-218.
Thompson, et al., "Cellular Uptake Mechanisms and Endosomal Trafficking of Supercharged Proteins", Chemistry & Biology, vol. 19, Issue 7, Jul. 27, 2012, 831-843.
Thompson, et al., "Engineering and Identifying Supercharged Proteins for Macromolecule Delivery into Mammalian Cells", Methods in Enzymology, vol. 503, 2012, 293-319.
Tolentino, et al., "Intravitreal Injection of Vascular Endothelial Growth Factor Small Interfering RNA Inhibits Growth and Leakage in a Nonhuman Primate, Laser-Induced Model of Choroidal Neovascularization", Retina, vol. 24, No. 4, Aug. 2004, 132-138.
Tsai, et al., "Dimeric CRISPR RNA-Guided FokI Nucleases for Highly Specific Genome Editing", Nature Biotechnology, vol. 32, No. 6, Jun. 2014, 569-577.
Uchegbu, et al., "Nanomedicines and Nanodiagnostics Come of Age", Journal of Pharmaceutical Sciences, vol. 102, Issue 2, Feb. 2013, 305-310.
Uchegbu, "Pharmaceutical Nanotechnology: Polymeric Vesicles for Drug and Gene Delivery", Journal Expert Opinion on Drug Delivery, vol. 3, Issue 5, Sep. 1, 2006, 629-640.
Uchegbu, et al., "Quaternary Ammonium Palmitoyl Glycol Chitosan—a New Polysoap for Drug Delivery", International Journal of Pharmaceutics, vol. 224, No. 1-2, Aug. 14, 2001, 185-199.
Uno, et al., "High-Density Lipoprotein Facilitates In Vivo Delivery of Alpha-Tocopherol—Conjugated Short-Interfering RNA to the Brain", Human Gene Therapy, vol. 22, Jun. 2011, 711-719.
Van Embden, et al., "Genetic Variation and Evolutionary Origin of the Direct Repeat Locus of *Mycobacterium tuberculosis* Complex Bacteria", J. Bacteriology, vol. 182, No. 9, May 2000, 2393-2401.
Wahlgren, et al., "Plasma Exosomes can Deliver Exogenous Short Interfering RNA to Monocytes and Lymphocytes", Nucleic Acid Research, vol. 40, No. 17, e130, May 22, 2012, 12 pages.
Wang, et al., "Genetic Screens in Human Cells Using the CRISPR/Cas9 System", Science, vol. 343, No. 6166, Jan. 3, 2014, 80-84.
Wang, et al., "One-Step Generation of Mice Carrying Mutations in Multiple Genes by CRISPR/Cas-Mediated Genome Engineering", Cell, vol. 153, No. 4, May 9, 2013, 13 pages.
Weintraub, "The New Gold Standard", Nature, vol. 495, Mar. 14, 2013, S14-S16.
Whitehead, et al., "The in-Vitro-In Vivo Translation of Lipid-Nanoparticles for Hepatocellular siRNA Delivery", ACS Nano, vol. 6, No. 8, Aug. 28, 2012, 6922-6929.
Winoto, et al., "A Novel, Inducible and T Cell-Specific Enhancer Located at the 3' End of the T Cell Receptor α Locus", The EMBO Journal, vol. 8, No. 3, 1989, 729-733.
Winzeler, et al., "Functional Characterization of the *S. Cerevisiae* Genome by Gene Deletion and Parallel Analysis", Science, vol. 285, No. 5429, Aug. 6, 1999, 901-906.
Wu, et al., "Genome-Wide Binding of the CRISPR Endonuclease Cas9 in Mammalian Cells", Nature Biotechnology, vol. 32, No. 7, Jul. 2014, 670-676.
Xia, et al., "siRNA-Mediated Gene Silencing in Vitro and in Vivo", Nature Biotechnology, vol. 20, Issue 10, Sep. 2002, 1006-1010.
Xie, et al., "RNA-Guided Genome Editing in Plants Using a CRISPR-Cas System", Molecular Plant, vol. 6, No. 6, Nov. 2013, 1975-1983.
Xu, et al., "Design of 240,000 Orthogonal 25mer DNA Barcode Probes", PNAS, vol. 106, No. 7, Feb. 17, 2009, 2289-2294.
Xu, et al., "Gene Targeting Using the Agrobacterium Tumefaciens-Mediated CRISPR-Cas System in Rice", Rice, vol. 7, No. 5, 2014, 4 pages.
Xu, et al., "Sequence Determinants of Improved CRISPR SgRNA Design", Genome Research, vol. 25, No. 8, Aug. 2015, 11 pages.
Young, et al., "Hollow Spherical Nucleic Acids for Intracellular Gene Regulation Based Upon Biocompatible Silica Shells", Nano Letters, vol. 12, Issue 7, Jul. 11, 2012, 3867-3871.
Zetsche, et al., "A Split-Cas9 Architecture for Inducible Genome Editing and Transcription Modulation", Nature Biotechnology, vol. 33, No. 2, Feb. 2015, 139-142.
Zetsche, et al., "Cpf1 is a Single RNA-Guided Endonuclease of a Class 2 CRISPR-Cas System", Cell, vol. 163, No. 3, Oct. 22, 2015, 14 pages.
Zhang, et al., "A Strategy for Increasing Drug Solubility and Efficacy through Covalent Attachment to Polyvalent DNA-Nanoparticle Conjugates", ACS Nano, vol. 5, No. 9, Sep. 27, 2011, 6962-6970.
Zhang, et al., "Antibody-linked Spherical Nucleic Acids for Cellular Targeting", Journal of the American Chemical Society, vol. 134, Issue 40, Oct. 10, 2012, 16488-16491.
Zhang, et al., "Lipid-Modified Aminoglycoside Derivatives for in vivo siRNA Delivery", Advanced Materials, vol. 25, No. 33, Sep. 6, 2013, 4641-4645.
Zhang, et al., "Structure-Based Prediction of Protein-Protein Interactions on a Genome-Wide Scale", Nature, vol. 490, Oct. 25, 2012, 556-560.
Zheng, et al., "Topical Delivery of siRNA-Based Spherical Nucleic Acid Nanoparticle Conjugates for Gene Regulation", Proceedings of the National Academy of Sciences, vol. 109, No. 30, Jul. 24, 2012, 11975-11980.
Zhou, et al., "Exploiting SNPs for Biallelic CRISPR Mutations in the Outcrossing Woody Perennial Populus Reveals 4-coumarate:CoA ligase Specificity and Redundancy", New Phytologist, vol. 208, Oct. 2015, 298-301.
Zimmerman, et al., "RNAi-Mediated Gene Silencing in Non-Human Primates", Nature Letters, vol. 441, May 4, 2006, 111-114.
Zou, "Intrathecal Lentiviral-Mediated RNA Interference Targeting PKCγ Attenuates Chronic Constriction Injury—Induced Neuropathic Pain in Rats", Human Gene Therapy, vol. 22, Apr. 2011, 465-475.
Zuker, et al., "Optimal Computer Folding of Large RNA Sequences Using Thermodynamics and Auxiliary Information", Nucleic Acids Research, vol. 9, No. 1, 1981, 133-148.

* cited by examiner

```
                           SEQUENCE LISTING

<160> NUMBER OF SEQ ID NOS: 39

<210> SEQ ID NO 1
<211> LENGTH: 40
<212> TYPE: DNA
<213> ORGANISM: Homo sapiens

<400> SEQUENCE: 1
aaatcgccac catggagacc agcagaaccg acaaaggcct                              40

<210> SEQ ID NO 2
<211> LENGTH: 20
<212> TYPE: DNA
<213> ORGANISM: Homo sapiens

<400> SEQUENCE: 2
gagaccagca gaaccgacaa                                                   20

<210> SEQ ID NO 3
<211> LENGTH: 40
<212> TYPE: DNA
<213> ORGANISM: Homo sapiens

<400> SEQUENCE: 3
aaatcgccac catgacggga gggcagggac gaaaaggcct                              40

<210> SEQ ID NO 4
<211> LENGTH: 20
<212> TYPE: DNA
<213> ORGANISM: Homo sapiens

<400> SEQUENCE: 4
cgggagggca gggcacgaaa                                                   20

<210> SEQ ID NO 5
<211> LENGTH: 40
<212> TYPE: DNA
<213> ORGANISM: Homo sapiens

<400> SEQUENCE: 5
aaatcgccac catgagggca cagaccccag ggagaggcct                              40

<210> SEQ ID NO 6
<211> LENGTH: 20
<212> TYPE: DNA
<213> ORGANISM: Homo sapiens

<400> SEQUENCE: 6
agggcacaga ccccagggag                                                   20

<210> SEQ ID NO 7
<211> LENGTH: 20
<212> TYPE: DNA
<213> ORGANISM: Homo sapiens

<400> SEQUENCE: 7
agggcgcaga ccccagggag                                                   20
```

```
<210> SEQ ID NO 8
<211> LENGTH: 20
<212> TYPE: DNA
<213> ORGANISM: Homo sapiens

<400> SEQUENCE: 8
agggcacgga ccccagggag                                               20

<210> SEQ ID NO 9
<211> LENGTH: 40
<212> TYPE: DNA
<213> ORGANISM: Homo sapiens

<400> SEQUENCE: 9
aaatcgccac catggagacc agcagaaccg acaaaggcct                         40

<210> SEQ ID NO 10
<211> LENGTH: 20
<212> TYPE: DNA
<213> ORGANISM: Homo sapiens

<400> SEQUENCE: 10
gagaccagca gaaccgacaa                                               20

<210> SEQ ID NO 11
<211> LENGTH: 20
<212> TYPE: DNA
<213> ORGANISM: Homo sapiens

<400> SEQUENCE: 11
gggaccagca gaaccgacaa                                               20

<210> SEQ ID NO 12
<211> LENGTH: 20
<212> TYPE: DNA
<213> ORGANISM: Homo sapiens

<400> SEQUENCE: 12
gagaccggca gaaccgacaa                                               20

<210> SEQ ID NO 13
<211> LENGTH: 40
<212> TYPE: DNA
<213> ORGANISM: Homo sapiens

<400> SEQUENCE: 13
aaatcgccac catgacggga gggcagggac gaaaaggcct                         40

<210> SEQ ID NO 14
<211> LENGTH: 20
<212> TYPE: DNA
<213> ORGANISM: Homo sapiens

<400> SEQUENCE: 14
cgggagggca gggcacgaaa                                               20

<210> SEQ ID NO 15
<211> LENGTH: 20
<212> TYPE: DNA
<213> ORGANISM: Homo sapiens

<400> SEQUENCE: 15
cgggagggcg gggcacgaaa                                               20
```

```
<210> SEQ ID NO 16
<211> LENGTH: 20
<212> TYPE: DNA
<213> ORGANISM: Homo sapiens

<400> SEQUENCE: 16 cggggggca gggcacgaaa                                                    20

<210> SEQ ID NO 17
<211> LENGTH: 40
<212> TYPE: DNA
<213> ORGANISM: Homo sapiens

<400> SEQUENCE: 17
aaatcgccac catggcgcaa cagagagggg agcgaggcct                             40

<210> SEQ ID NO 18
<211> LENGTH: 20
<212> TYPE: DNA
<213> ORGANISM: Homo sapiens

<400> SEQUENCE: 18
gcgcaacaga gaggggagcg                                                   20

<210> SEQ ID NO 19
<211> LENGTH: 20
<212> TYPE: DNA
<213> ORGANISM: Homo sapiens

<400> SEQUENCE: 19
gcgcaacagg gaggggagcg                                                   20

<210> SEQ ID NO 20
<211> LENGTH: 20
<212> TYPE: DNA
<213> ORGANISM: Homo sapiens

<400> SEQUENCE: 20
gcgcgacaga gaggggagcg                                                   20

<210> SEQ ID NO 21
<211> LENGTH: 40
<212> TYPE: DNA
<213> ORGANISM: Homo sapiens

<400> SEQUENCE: 21
aaatcgccac catgagggca cagaccccag ggagaggcct                             40

<210> SEQ ID NO 22
<211> LENGTH: 20
<212> TYPE: DNA
<213> ORGANISM: Homo sapiens

<400> SEQUENCE: 22
agggcacaga ccccagggag                                                   20

<210> SEQ ID NO 23
<211> LENGTH: 20
<212> TYPE: DNA
<213> ORGANISM: Homo sapiens

<400> SEQUENCE: 23
agggcgcaga ccccagggag                                                   20
```

<210> SEQ ID NO 24
<211> LENGTH: 20
<212> TYPE: DNA
<213> ORGANISM: Homo sapiens

<400> SEQUENCE: 24
agggcacgga ccccagggag                                                    20

<210> SEQ ID NO 25
<211> LENGTH: 40
<212> TYPE: DNA
<213> ORGANISM: Homo sapiens

<400> SEQUENCE: 25
aaatcgccac catgacaggg ggagcgaaag agaaaggcct                              40

<210> SEQ ID NO 26
<211> LENGTH: 20
<212> TYPE: DNA
<213> ORGANISM: Homo sapiens

<400> SEQUENCE: 26
caggggggag cgaaagagaa                                                    20

<210> SEQ ID NO 27
<211> LENGTH: 20
<212> TYPE: DNA
<213> ORGANISM: Homo sapiens

<400> SEQUENCE: 27 caggggggggg cgaaagagaa                                                   20

<210> SEQ ID NO 28
<211> LENGTH: 20
<212> TYPE: DNA
<213> ORGANISM: Homo sapiens

<400> SEQUENCE: 28
caggggggag cgaaagagag                                                    20

<210> SEQ ID NO 29
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 29
aaatcgccac catgttttgt tcagccg                                            27

<210> SEQ ID NO 30
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 30
tattgttcgg c                                                             11

<210> SEQ ID NO 31
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 31
aaaacaagtc ggcataacaa                                              20

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 32
aaatcgccac catgcggc                                                18

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
gcttacgccg tgcttataat                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
aggtaagtgt cgctgcgggc                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
ttttgttcag ccgtattgtt                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
cgaatgcggc acgaatatta                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
gttaatagag cgggagtttt                                              20
```

```
<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
gggtcgacgg gtaagatgat                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
taaaacgtgt agttgggagt                                            20
```

METHODS AND COMPOSITIONS FOR STUDYING CELL EVOLUTION

CROSS-REFERENCE TO RELATED APPLICATIONS

This application is a U.S. National Stage of International Application No. PCT/US2018/058519, filed on Oct. 31, 2018, which claims the benefit of U.S. Provisional Application No. 62/579,858, filed on Oct. 31, 2017. The entire contents of the above-identified applications are hereby fully incorporated herein by reference.

TECHNICAL FIELD

The subject matter disclosed herein is generally directed to methods and compositions for tagging cells of interest, tracking evolution of the tagged cells, and recovering the original tagged cells for further study.

REFERENCE TO AN ELECTRONIC SEQUENCE LISTING

The contents of the electronic sequence listing (BROD_2150WP_ST25.txt"; Size is 7 Kilobytes and it was created on Oct. 31, 2018) is herein incorporated by reference in its entirety.

BACKGROUND

Elucidating the biological processes underlying evolutionary selection is fundamental to our understanding of the genesis of human disease and its response to therapy. However, a comprehensive analysis of both the phenotypic and genomic underpinnings of evolutionary fitness has been precluded by the high cost, extensive labor and cell destructive nature of single-cell phenotypic and genetic characterization methods.

Tracking sub-clones and their progeny ("lineages") within a population of cells is essential to understanding the dynamics of evolutionary selection. Diverse libraries of inert DNA barcodes have provided a scalable methodology for tracking individual cells, but preclude phenotypic and genetic characterization of the drivers of evolutionary dynamics. Single-cell characterization methods have facilitated characterization, but are challenging to scale appropriately due to their high cost, inability to preserve cell viability, reduced resolution and incompatibility with current barcoding strategies. Moreover, studying the lineages that are not selected for is impossible using current methods. As a result, the determinants of drug sensitivity, clonal non-selection and unfit epigenetic states are precluded from discovery and the ability to capitalize on them is blunted. Thus, a bottleneck in defining the genetic and phenotypic basis of evolutionary selection is the lack of an experimental system that permits tracking, selection, and viable recovery at any stage of evolution of cells from specific lineages, permitting phenotypic and genomic characterization of these cells and their progeny. A novel methodology is crucial to move from passive population-level observations of cancer evolution to testing clone specific, mechanistic hypotheses.

SUMMARY

In certain example embodiments, the present invention provides for the simultaneous tracking of populations of cells and capacity to isolate specific sub-populations of viable or unviable cells (EvoSeq). In certain embodiments, a library of tagged cells is expanded and an original untreated population preserved. Barcodes are identified in a treated fraction of the library of tagged cells and barcoded cells may be isolated from the original untreated population based on enrichment or depletion of the barcodes in the treated population. The approach uses guide RNA library sequences as barcodes to track and isolate specific sub-populations of cells. Cells can be isolated by introduction of reporter constructs specific for the guide sequence barcodes. This approach can facilitate the elucidation of the molecular and phenotypic basis of any evolutionary selection process, including the induction of pluripotent stem cell populations, tumor formation in animal models, nascent cell line model generation and phenotypic penetrance of functional genomics screens.

In one aspect, the present invention provides for a polynucleotide reporter construct comprising one or more CRISPR-Cas guide molecule target loci, a first type of one or more markers that are out-of-frame, and a second type of one or more markers that are in-frame.

In another aspect, the present invention provides for a reporter system comprising: a polynucleotide reporter construct comprising one or more guide molecule target loci, a first type of one or more markers that are out-of-frame, and a second type of one or more markers that are in-frame; a CRISPR-Cas effector protein, or a nucleotide sequence encoding the CRISPR-Cas effector protein; a library comprising a set of guide molecule constructs each construct encoding a different guide sequence, the guide sequence comprising a barcode sequence and each guide sequence configured to guide the CRISPR-Cas effector protein to one of the one or more target loci of the polynucleotide reporter construct.

In another aspect, the present invention provides for a method of selecting one or more cells from mixed populations of cells comprising: a) tagging individual cells in a mixed population of cells with a guide molecule construct encoding a guide sequence from a library of constructs encoding different guide sequences, each guide sequence encoding a unique barcode sequence, and each guide sequence configured to guide a CRISPR-Cas effector protein to a target loci of a polynucleotide reporter construct, the polynucleotide reporter construct comprising the one or more target loci, a first type of one or more markers that are out-of-frame, and a second type of one or more markers that are in frame; b) exposing the mixed population of cells to one or more perturbations; c) determining cells of interest by sequencing a portion of the mixed population of cells and assessing a ratio of the different barcode sequence counts; d) selecting the cells of interest by introducing polynucleotide reporter constructs comprising target loci for the guide sequences comprising the one or more barcodes of interest and a CRISPR-Cas effector protein, or inducing expression within the cells of a CRISPR-Cas effector protein, wherein the guide sequence expressed in cells having the barcodes of interest will guide the CRISPR-Cas effector protein to the target loci of the polynucleotide reporter construct, and wherein the CRISPR-Cas effector protein will make a frame shift edit at the target loci that shifts the first type of markers in frame such that the first type of one or more markers are expressed, and such that the second type of one or more markers are shifted out-of-frame such that second type of markers are no longer expressed; and e) retrieving the cells of interest based on expression of the first type of one or more markers.

In certain embodiments, the first type and second type of markers according to the construct, system, or method of any of the proceeding aspects are selectable markers, such as antibiotic resistance markers, affinity tags, optically-detectable markers, chemiluminescent detectable markers, fluorescently detectable markers, surface markers or a combination thereof. The first type of marker may be a first fluorescently detectable marker detectable at a first wavelength, and the second type of marker may be a second fluorescently detectable marker detectable at a second wavelength.

In certain embodiments, the polynucleotide construct according to the construct, system, or method of any of the proceeding aspects comprises an out-of-frame stop codon between the first type of marker and the second type of marker.

In certain embodiments, the polynucleotide reporter construct, the guide molecule construct, and/or the polynucleotide encoding the CRISPR-Cas protein according to the construct, system, or method of any of the proceeding aspects are operably linked to a regulatory element. The regulatory element may be a promoter, and wherein the promoter may be the same or different.

In certain embodiments, the construct according to the construct, system, or method of any of the proceeding aspects further encodes a stop codon upstream of the target loci.

In certain embodiments, the one or more perturbations according to the construct, system, or method of any of the proceeding aspects may be one or more genetic or RNA perturbations, one or more chemical perturbations, one or more physical perturbations, or a combination thereof. The one or more genetic or RNA perturbations may comprise one or more gene knock-ins; one or more gene knock-outs, one or more nucleotide insertions, deletions, or substitutions; one or more transpositions; or one or more inversions. The one or more physical perturbations may comprise different temperatures, pH, growth media conditions, atmospheric $CO_2$ concentrations, atmospheric $O_2$ concentrations, and/or sheer stresses. The one or more chemical perturbations may comprise exposing a set of samples comprising the mixed population of cells to a different chemical compound or combination of chemical compounds, a different concentration of a same chemical compound or combination of chemical compounds, or different concentrations of different chemical compounds or combinations of chemical compounds. The chemical compound or combination of chemical compounds may be a therapeutic agent or combination of therapeutic agents.

In certain embodiments, the cells of interest according to the construct, system, or method of any of the proceeding aspects are determined by identifying a phenotype of interest, such as, changes in growth characteristics, morphology, motility, cell death, cell-to-cell contacts, antigen presentation and synapsing, and interactions with patterned substrates. The cells of interest may be cells that are resistant to the one or more genetic or RNA perturbations, or to the one or more therapeutic agents or combinations of therapeutic agents.

In certain embodiments, the cells according to the construct, system, or method of any of the proceeding aspects are retrieved using fluorescence-activated cell sorting.

In another aspect, the present invention provides for a population of cells comprising a plurality of cells, each of the plurality of cells comprising a guide molecule construct from a set of guide molecule constructs, each construct encoding a different guide sequence, the guide sequence comprising a barcode sequence and each guide sequence configured to guide a CRISPR-Cas effector protein to one or more target loci of a reporter construct. In certain embodiments, the reporter construct comprises one or more guide molecule target loci specific for a guide sequence in the plurality of cells, a first type of one or more markers that are out-of-frame, and a second type of one or more markers that are in-frame.

In certain embodiments, the method according to any embodiment herein provides for tagging cells with a construct comprising a barcode, wherein the barcode comprises a guide sequence and wherein cells are retrieved by introducing a reporter construct and CRISPR system to the cells.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

Figure 1:
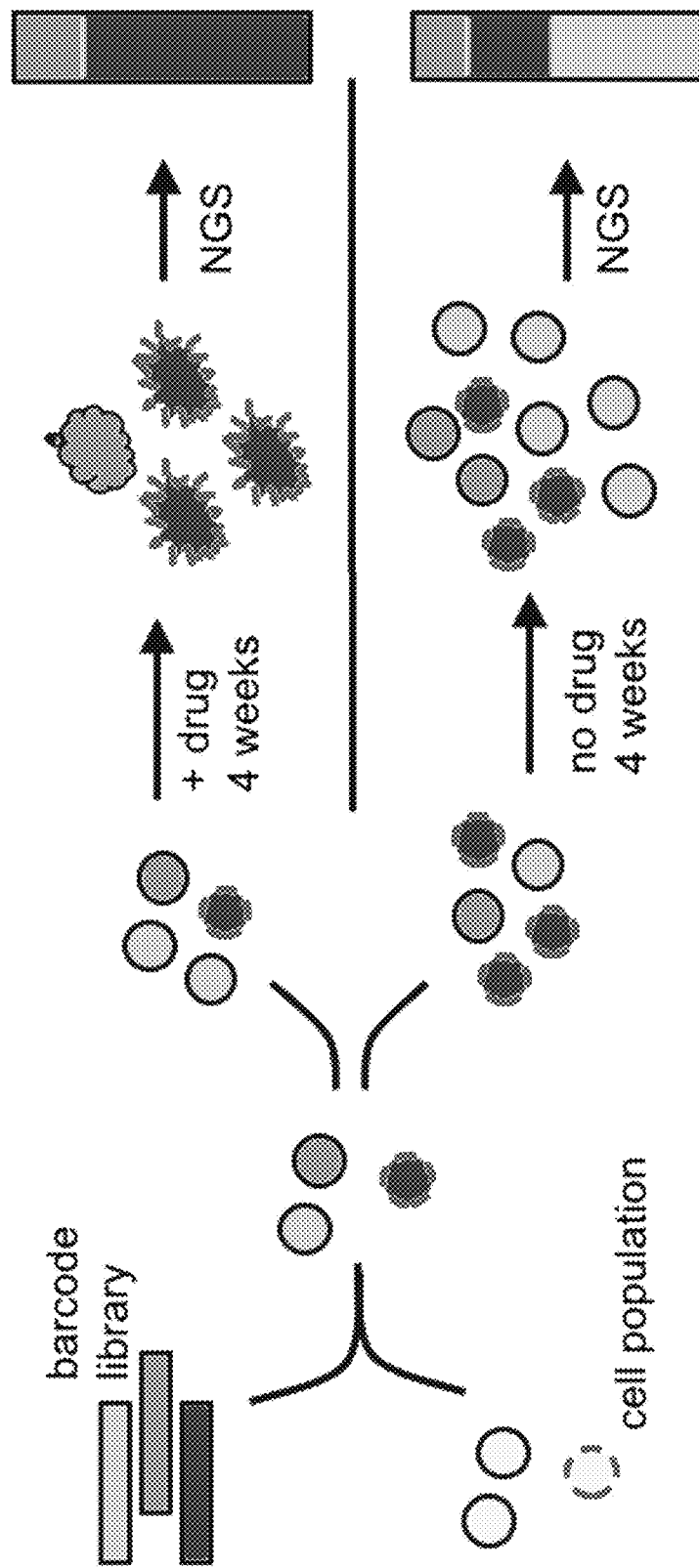
FIG. 1—Schematic showing tracking of cancer cells using a barcoded cell library.
Figure 2:
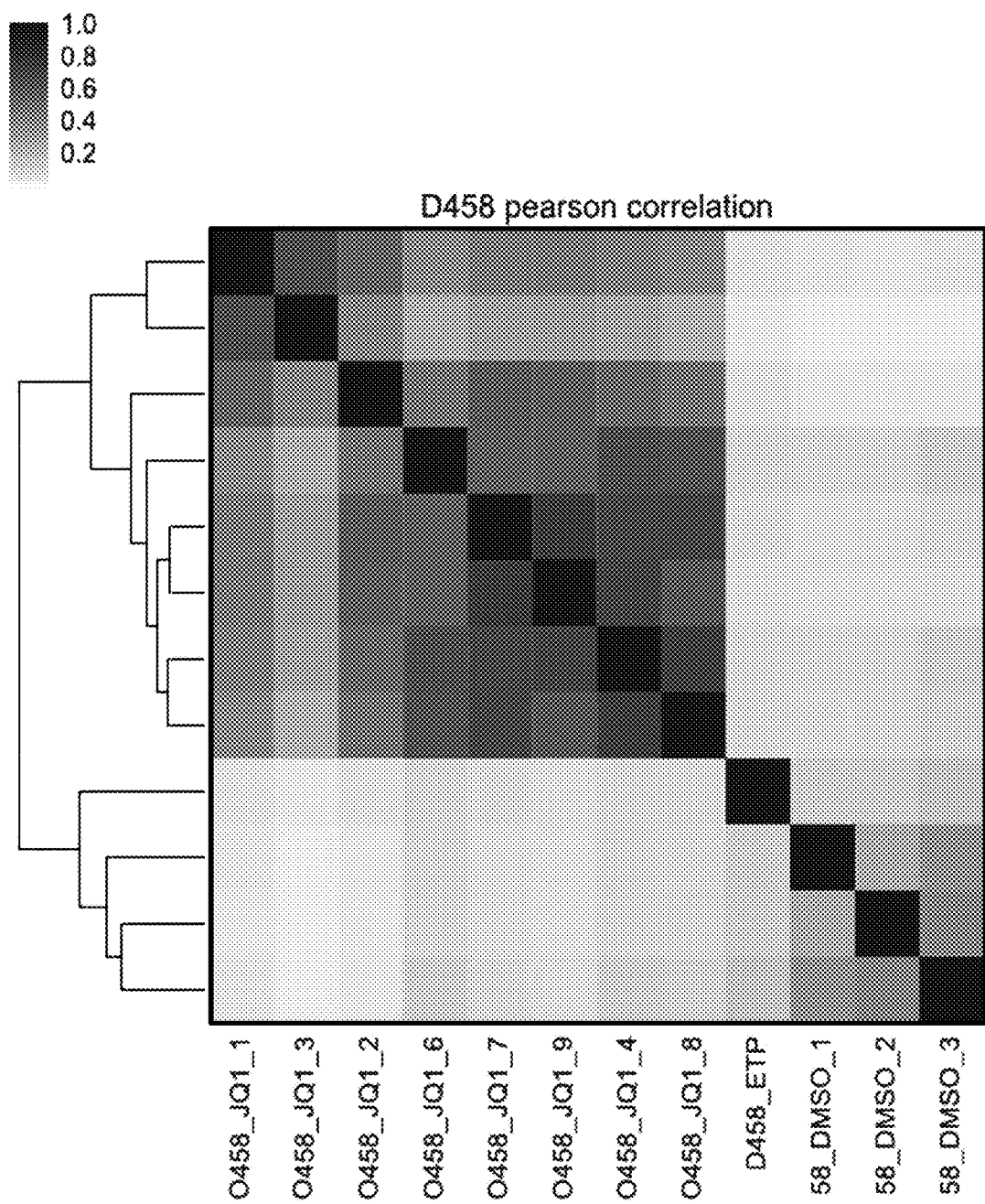
FIG. 2—Graph showing that barcoded cells cluster together with other replicates that have been passaged with BET-bromodomain inhibitors.
Figure 3:
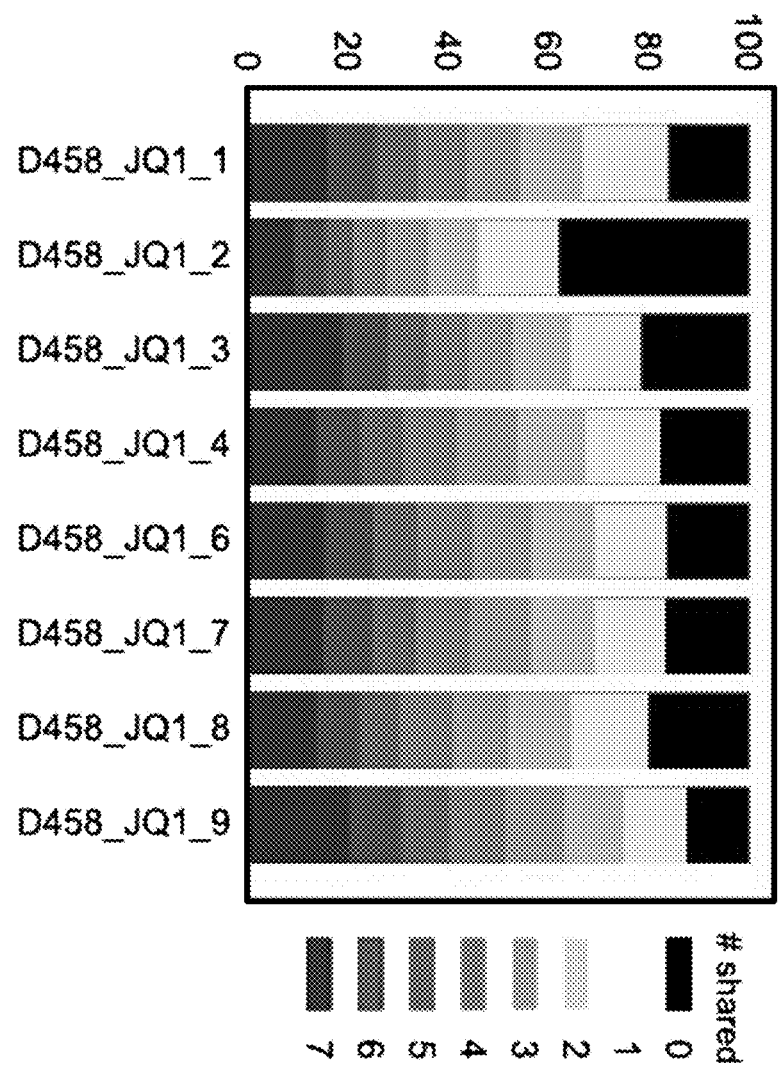
FIG. 3—Shows that enriched barcodes are shared across JQ1 treated replicates.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to International patent application serial number PCT/US2016/038234 filed Jun. 17, 2016 and published as WO2016205745A2.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide for the simultaneous tracking of populations of cells and capacity to isolate specific sub-populations of viable or unviable cells (EvoSeq). Evo-Seq is a barcoding technology that has these capabilities. The embodiments disclosed here label individual cells in a mixed population of cells by delivering to the cells constructs encoding guide sequences, the guide sequences further encoding a unique barcode sequence. The barcode sequence may be used to identify individual cells and clones thereof. The methodology allows isolation and comparative analysis of specific populations of cells at any stage of evolution. These cells can then be characterized by downstream functional assays, such as phenotypic characterization, genetic perturbation, or small molecule screens, thus enabling a focused analysis of how lineage features, as opposed to the features of the bulk population, evolve during selection. For example, through embodiments disclosed herein, a lineage found to be depleted in response to a selection pressure could be recovered prior to implementing that pressure and causative features identified through comparison to populations that survived selection pressure.

The analysis of genetically heterogeneous cell populations is complicated by the fact that many biological assays are destructive, making it difficult to isolate cells with particular properties for further study and use. For example, cells originating from a patient tumor may carry different mutations and chromosomal arrangements, leading to different properties, e.g., resistance to chemotherapy. Techniques such as RNA and protein analysis may reveal key signatures of resistant cells, e.g., an aberrant epigenetic state, but destroy the cells, thus precluding further experiments on the same cells. Traditionally, this limitation has been circumvented in dividing cell populations by isolating individual cells, e.g., in a multiwell plate, expanding the cells, and splitting the cells for downstream use. However, this process is laborious (each cell must be handled individually), slow (typically a month to expand cells), and low throughput. Furthermore, many cell types are not amenable to expansion from single cells, which may cause cell death or profound changes to cell physiology. Recently, the introduction of unique DNA barcodes into a cell population has partially alleviated this difficulty. Barcoded cells are expanded, split into parallel selection-based assays, and after each assay barcodes are counted by next-generation sequencing (Nolan-Stevaux, Olivier et al. "Measurement of cancer cell growth heterogeneity through lentiviral barcoding identifies clonal dominance as a characteristic of in vivo tumor engraftment." *PloS one* 8.6 (2013)). However, this does not address the goal of retrieving particular sub-populations (such as the descendants of an initial resistant cell), and is limited to selection-based assays with a simple readout obtainable by counting barcodes as a proxy for cells.

Frameshift Reporter Constructs

The frameshift constructs are generated to recover cells from a recovery population expressing guide sequences of interest. The recovery constructs may include one or more out of frame detectable markers, such that targeting CRISPR to the construct by the guide sequence of interest creates an indel capable of shifting the detectable marker to the correct frame. In certain embodiments, the frameshift construct may include two different detectable markers type, with one or more copies of each type per construct. One marker may be in frame and one marker out of frame, such that targeting CRISPR to the construct by the guide sequence of interest creates an indel capable of shifting the in frame detectable marker out of frame and shifting the out of frame detectable marker to the correct frame. Thus, cells can be advantageously recovered by detecting the loss of expression of one marker and gain of expression of a second marker. The markers preferably can be detected at different wavelengths. The frame shift reporter may include a translation stop signal upstream of the start codon and optionally the Kozak sequence of the out of frame detectable marker. Not being bound by a theory, the translation stop sequence prevents translation of the out of frame marker without indel formation. Upon indel formation the translation stop signal is inactivated and the marker can be expressed. The in frame detectable marker is the first ATG translated before indel formation. The reporter construct can also include an out of frame translation stop signal upstream of the in frame detectable marker, such that upon indel formation the stop signal is in frame and the marker is not expressed (see, e.g., FIGS. 15, 24-27).

Components of the reporter may include a) a constitutive mammalian promoter (e.g., EFS, EF1a); b) 3× STOP, encodes stop codons in all 3 reading frames to suppress upstream translation; c) guide spacer, contains the barcode-specific sequence (for CRISPR-Cas9, this includes a 3' NGG PAM); d) T2A TM, self-cleaving 2A linker, silent nucleotide substitutions to remove ATG start codons; e) GFP TM, contains silent and amino acid substitutions to remove ATG start codons; f) shift of 2 bp, changing downstream reading frame; g) P2A TM, similar to T2A TM but derived from different 2A linker; h) Puro TM, contains silent substitutions to remove ATG start codons (applying puromycin before barcode targeting selects for cells expressing the Puro-mCherry frame, not the GFP frame); i) T2A, nucleotide sequence silently modified from T2A TM to avoid lentiviral recombination; and k) mCherry fluorescent reporter. The reporter may also include any of the following. (A) An upstream ORF embedded in a bait sequence. Targeting the ORF leads to an indel, causing translation to shift to the downstream reporter ORF. The ATG start codon should be preceded by an RCC Kozak sequence, limiting the complexity in the critical PAM-proximal bases. Cryptic start/stop codons can be avoided by generating the bait with a 3 letter alphabet, e.g., V=A/C/G. An alternate bait could be encoded in the antisense direction, at the complexity cost of fixing two additional bases (antisense PAM). Enhanced nonsense mediated decay (NMD) may result from termination far upstream of an exon-exon junction. (B) A bicistronic out-of-frame reporter switches translation from GFP to mCherry if a +2/−1 indel occurs in a bait region after the start codon. Multiple guide target sequences could be placed in tandem. The bases around the cut site could be designed based on existing indel datasets to bias repair towards a +2/−1 indel. The 2A sequences match the frame of the subsequent reporter. (C) Mutate splice acceptor, switching cells from GFP to RFP.

Methodology for Cell Sorting

In another aspect, the embodiments disclosed here are direct to sorting cells using the reporter constructs described above. Individual cells may be tagged using guide sequences from a library of input guides sequences that are delivered, for example, by a viral vector, each guide sequence comprising a unique barcode. The tagged cells may then be expanded and split into a test population and recovery population. Optionally, the recovery population may be cryogenically preserved. The test population may then be exposed to different perturbations (e.g. drug regimens, growth factors, cytokines, chemical and/or physical perturbations) over a set period of time. Cells of interest may be identified by sequencing the barcodes across multiple replicates. For example, the replicates may be obtained by splitting the test cell population in to separate sub-populations during assay growth. The relative abundance of the sequenced barcodes may then be compared to the barcodes of the input library, with depleted barcodes indicating a survival or growth disadvantage under the test conditions, and those barcodes remaining identifying cells with a survival or growth advantage under the perturbation conditions. Frameshift reporters, such as those described above, and CRISPR-Cas ribonucleoprotein complex (or a nucleotide encoding a CRISPR-Cas protein and guide sequence) may then be delivered to the recovery population to select cells that expression guide sequences encoding the barcode of interest. In certain example embodiments, the recovery population may be engineered to express a CRISPR-Cas protein. Expression of the CRISPR-Cas protein may be inducible. Otherwise, the CRISPR-Cas protein or a construct encoding the CRISPR-Cas protein is delivered to the recovery population. CRISPR-Cas proteins and guide sequence suitable for use in the present invention are discussed in more detail below. Cells expressing guide sequences comprising the guide sequence of interest may then be isolated by a selection protocol, e.g. FACS based on the detectable markers of the frameshift reporter (e.g., mCherry, GFP expression). Cell expressing guide sequences comprising the barcodes of interest will direct the Cas effector protein to the target sequence on the reporter construct where the Cas protein will introduce a frameshift edit, thereby changing expression of the first and second type of selectable markers. The change of expression in the first and second selectable markers may then be used to select out the cells of interest from the recovery population.

The above ordering of steps is exemplary. Certain steps may be performed in a different sequence, or be combined together in a single step, while still providing an ability to select for and isolate the cells of interest.

Populations of Cells

In certain embodiments, the population of cells can be cancer cells. In certain embodiments, the evolution of cancer cells from initiation through establishment of in vivo models can be performed. The cancer cells may be established cell lines or patient derived. In certain embodiments, the population of cells can be normal cells, thus allowing the study evolution and/or differentiation of normal cells, including immune cells and stem cells.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells including, e.g., thymocytes, Th or Tc; Th1, Th2, Th17, Thαβ, CD4+, CD8+, effector Th, memory Th, regulatory Th, CD4+/CD8+ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

In certain embodiments, the present invention may be used to understand differences in responses of individual clones following genetic perturbation. For example, to determine why some clones in a pool of cells infected with a specific ORF exhibit a selective phenotype (such as proliferation) while others do not.

Detectable Markers

In certain embodiments, the detectable marker is a fluorescent protein such as green fluorescent protein (GFP), enhanced green fluorescent protein (EGFP), red fluorescent protein (RFP), blue fluorescent protein (BFP), cyan fluorescent protein (CFP), yellow fluorescent protein (YFP), mCherry, tdTomato, DsRed-Monomer, DsRed-Express, DSRed-Express2, DsRed2, AsRed2, mStrawberry, mPlum, mRaspberry, HcRed1, E2-Crimson, mOrange, mOrange2, mBanana, ZsYellow1, TagBFP, mTagBFP2, Azurite, EBFP2, mKalamal, Sirius, Sapphire, T-Sapphire, ECFP, Cerulean, SCFP3A, mTurquoise, mTurquoise2, monomelic Midoriishi-Cyan, TagCFP, niTFP1, Emerald, Superfolder GFP, Monomeric Azami Green, TagGFP2, mUKG, mWasabi, Clover, mNeonGreen, Citrine, Venus, SYFP2, TagYFP, Monomeric Kusabira-Orange, mKOk, mK02, mTangerine, mApple, mRuby, mRuby2, HcRed-Tandem, mKate2, mNeptune, NiFP, mkeima Red, LSS-mKate1, LSS-mKate2, mBeRFP, PA-GFP, PAmCherryl, PATagRFP, TagRFP6457, IFP1.2, iRFP, Kaede (green), Kaede (red), KikGR1 (green), KikGR1 (red), PS-CFP2, mEos2 (green), mEos2 (red), mEos3.2 (green), mEos3.2 (red), PSmOrange, Dronpa, Dendra2, Timer, AmCyanl, or a combination thereof. In certain embodiments, the detectable marker is a cell surface marker. In other instances, the cell surface marker is a marker not normally expressed on the cells, such as a truncated nerve growth factor receptor (tNGFR), a truncated epidermal growth factor receptor (tEGFR), CD8, truncated CD8, CD19, truncated CD19, a variant thereof, a fragment thereof, a derivative thereof, or a combination thereof.

Nucleic Acid Barcode, Barcode, and Unique Molecular Identifier (UMI)

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin.

The term "barcode" as used herein, also refers to any unique, non-naturally occurring, nucleic acid sequence that may be used to identify the originating source of a nucleic acid fragment. Such barcodes may be sequences including but not limited to about 20 base pair sequences. Although it is not necessary to understand the mechanism of an invention, it is believed that the barcode sequence provides a high-quality individual read of a barcode associated with a single cell, a viral vector, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In certain embodiments, where the sequencing library comprises amplified cDNA or PCR amplification is used for enriching barcoded cDNA molecules, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No. 11, 163-166). Not being bound by a theory, the UMI's are designed such that assignment to the original can take place despite up to 4-7 errors during amplification or sequencing.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume (e.g., cell), having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

As disclosed herein, unique nucleic acid identifiers are used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www.

drmr.com/abcon). In certain embodiments, barcode tagging can occur via a barcode receiving adapter associate with (for example, attached to) a target molecule, as described herein.

Target molecules can be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SBS3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type A nucleic acid identifier can further include a unique molecular identifier and/or additional barcodes specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semisolid support can be added to the discreet volume sequentially after introduction of the target molecule pool), such that the precise combination of conditions to which a given target molecule was exposed can be subsequently determined by sequencing the unique molecular identifiers associated with it.

Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites. A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing. A nucleic acid target molecule labeled with a barcode (for example, an origin-specific barcode) can be sequenced with the barcode to produce a single read and/or contig containing the sequence, or portions thereof, of both the target molecule and the barcode.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a specific-binding agent after the specific-binding agent binds to a target molecule or a tag (for example, an encoded polypeptide identifier element cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which discrete volumes.

Barcode Adapters

In some embodiments, the target molecule is attached to an origin-specific barcode receiving adapter, such as a nucleic acid. In some examples, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang) capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a discreet volume of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

Sequencing

Any method of sequencing known in the art can be used before and after isolation. In certain embodiments, a sequencing library is generated and sequenced.

The terms "depth" or "coverage" as used herein refers to the number of times a nucleotide is read during the sequencing process. In regards to single cell RNA sequencing, "depth" or "coverage" as used herein refers to the number of mapped reads per cell. Depth in regards to genome sequencing may be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy.

The terms "low-pass sequencing" or "shallow sequencing" as used herein refers to a wide range of depths greater than or equal to 0.1× up to 1×. Shallow sequencing may also refer to about 5000 reads per cell (e.g., 1,000 to 10,000 reads per cell).

The term "deep sequencing" as used herein indicates that the total number of reads is many times larger than the length of the sequence under study. The term "deep" as used herein refers to a wide range of depths greater than 1× up to 100×. Deep sequencing may also refer to 100× coverage as compared to shallow sequencing (e.g., 100,000 to 1,000,000 reads per cell).

The term "ultra-deep" as used herein refers to higher coverage (>100-fold), which allows for detection of sequence variants in mixed populations.

In certain embodiments, a sequencing library is provided that is configured for sequencing by using next generation technologies. Methods for constructing sequencing libraries are known in the art (see, e.g., Head et al., Library construction for next-generation sequencing: Overviews and challenges. Biotechniques. 2014; 56(2): 61-77). In certain embodiments, the library members (e.g., cDNA) may include sequencing adaptors that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Ronaghi et al. (Analytical Biochemistry 1996 242: 84-9); Shendure et al. (Science 2005 309: 1728-32); Imelfort et al. (Brief Bioinform. 2009 10:609-18); Fox et al. (Methods Mol. Biol. 2009; 553:79-108); Appleby et al. (Methods Mol. Biol. 2009; 513:19-39); and Morozova et al. (Genomics. 2008 92:255-64), which are incorporated by reference for the general descriptions of the methods and the particular steps of the methods, including all starting products, reagents, and final products for each of the steps. In certain embodiments, isolated product may contain sequences that are compatible with use in, e.g., Illumina's reversible terminator method, Roche's pyrosequencing method (454), Life Technologies' sequencing by ligation (the SOLiD platform) or Life Technologies' Ion Torrent platform, as described above.

In some embodiments, the invention comprises 3' digital gene expression (DGE). DGE allows preparation of RNA-seq libraries from limited amounts of RNA template (e.g., single cells) across a large population of samples. DGE converts poly(A)+ mRNA to cDNA decorated with molecular barcodes. This method enables very high levels of sample multiplexing. The process can mark transcripts of a single cell with the same barcode and also uniquely marks each individual transcript molecule with Unique Molecular Indices (UMIs), which essentially barcode each input transcript. UMIs can overcome the effects of bias from library construction or amplification steps that affect other approaches. This method allows for the identification and quantification of transcripts.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-6'73, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

CRISPR Systems

The embodiments disclosed herein may utilize a large number of different CRISPR-Cas systems. In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen, Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters—especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the (3-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoide cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl (cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem loop regions, and the seed region. For Cas13 guide, in certain embodiments, the modification is not in the 5'-handle of the stem loop regions. Chemical modification in the 5'-handle of the stem loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl (cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemicially modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methylguanosine, 2'-O-methyl 3'phosphorothioate (MS), S-constrained ethyl (cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loop or optimized secondary structures. In particular embodiments, the direct repeat has a minimum length of 16 nts and a single stem loop. In further embodiments the direct repeat has a length longer than 16 nts, preferably more than 17 nts, and has more than one stem loop or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stem loop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y base pairing sequence (e.g., as to length) is tolerated, so long as the secondary structure of the entire guide molecule is preserved. In one aspect, the loop that connects the stem made of X:Y base pairs can be any sequence of the same length (e.g., 4 or 5 nucleotides) or longer that does not interrupt the overall secondary structure of the guide molecule. In one aspect, the stem loop can further comprise, e.g. an MS2 aptamer. In one aspect, the stem comprises about 5-7 bp comprising complementary X and Y sequences, although stems of more or fewer base pairs are also contemplated. In one aspect, non-Watson Crick base pairing is contemplated, where such pairing otherwise generally preserves the architecture of the stem loop at that position.

In particular embodiments the natural hairpin or stem loop structure of the guide molecule is extended or replaced by an extended stem loop. It has been demonstrated that extension of the stem can enhance the assembly of the guide molecule with the CRISPR-Cas proten (Chen et al. Cell. (2013); 155(7): 1479-1491). In particular embodiments the stem of the stem loop is extended by at least 1, 2, 3, 4, 5 or more complementary base pairs (i.e. corresponding to the addition of 2, 4, 6, 8, 10 or more nucleotides in the guide molecule). In particular embodiments these are located at the end of the stem, adjacent to the loop of the stem loop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stem loop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, 02 concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm2. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/r52), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027. abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www-.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc. (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al. 1998 Journal of Magnetic Resonance Imaging Vol. 8, No. 1, pp. 136-142. Another form of focused ultrasound is high intensity focused ultrasound (HIFU) which is reviewed by Moussatov et al. in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched base pairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, TJ., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science Dec. 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse); and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015);

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527 (7577):192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., *Molecular Cell*, 60(3), 385-397 doi: 10.1016/j.molcel.2015.10.008 Epub Oct. 22, 2015.

*Rationally engineered Cas9 nucleases with improved specificity*, Slaymaker et al., Science 2016 Jan. 1 351 (6268): 84-88 doi: 10.1126/science.aad5227. Epub 2015 Dec. 1.

Gao et al., "Engineered Cpf1 Enzymes with Altered PAM Specificities," bioRxiv 091611; doi: http://dx.doi.org/10.1101/091611 (Dec. 4, 2016).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multi-nucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al. (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al. (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

The methods and tools provided herein are may be designed for use with "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 15, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S.

application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

In certain example embodiments, the Cas protein is Cas9 or an orthologue thereof, an engineered Cas9, Cpf1 ortholog thereof, an engineered Cpf1, a naturally occurring or engineered single strand or double strand nickase. In certain example embodiments, the nickase is a CRISPR-Cas9$^{D10A}$ nickase. In certain example embodiments, the Cas protein is a Cpf1 variant with altered PAM specificities such as those disclosed in Gao et al. Nature Biotechnology, 2017. 35(8): 789-792.

Kits

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

The present invention advantageously provides for isolating and culturing subpopulations of cells with interesting, stable phenotypes by tagging cells with a DNA barcode comprising a guide sequence. The present invention is especially advantageous when the subpopulations are rare (<1%) at time points of interest (e.g., resistant cells before adding drug). Applicants have also unexpectedly determined that the subpopulations have a stable phenotype and behave reproducibly after >15 divisions+freeze-thaw.

The invention is further described in the following examples, which do not limit the scope of the invention described in the claims.

EXAMPLES

Example 1—Systems and Methods for Efficient Isolation of Clonal Sub-Populations

The analysis of genetically heterogeneous cell populations is complicated by the fact that many biological assays are destructive, making it difficult to isolate cells with particular properties for further study and use. For example, cells originating from a patient tumor may carry different mutations and chromosomal arrangements, leading to different properties, e.g., resistance to chemotherapy. Techniques such as RNA and protein analysis may reveal key signatures of resistant cells, e.g., an aberrant epigenetic state, but destroy the cells, thus precluding further experiments on the same cells. Traditionally, this limitation has been circumvented in dividing cell populations by isolating individual cells, e.g., in a multiwell plate, expanding the cells, and splitting the cells for downstream use. However, this process is laborious (each cell must be handled individually), slow (typically a month to expand cells), and low throughput. Furthermore, many cell types are not amenable to expansion from single cells, which may cause cell death or profound changes to cell physiology.

Figure 4:
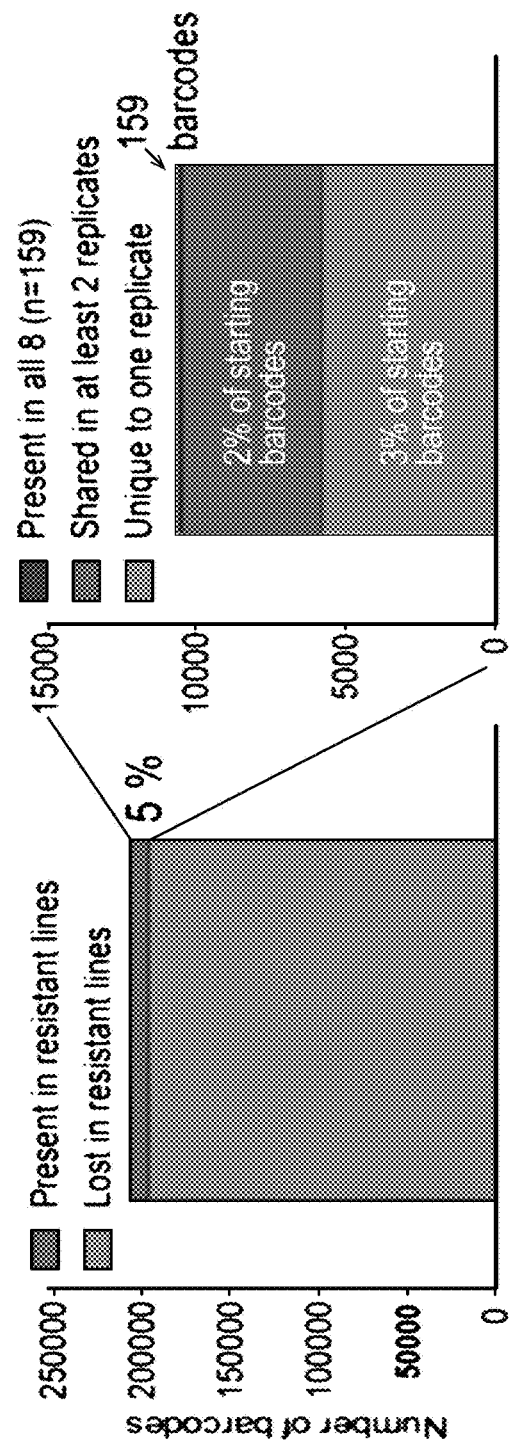
FIG. 4—Percentage of barcodes that persist following treatment with JQ1. Only 5% of barcodes persist after JQ1 treatment, but these same barcodes tend to be recovered in replicate experiments—indicating JQ1 resistance is a predetermined feature of those cells.
Figure 5:
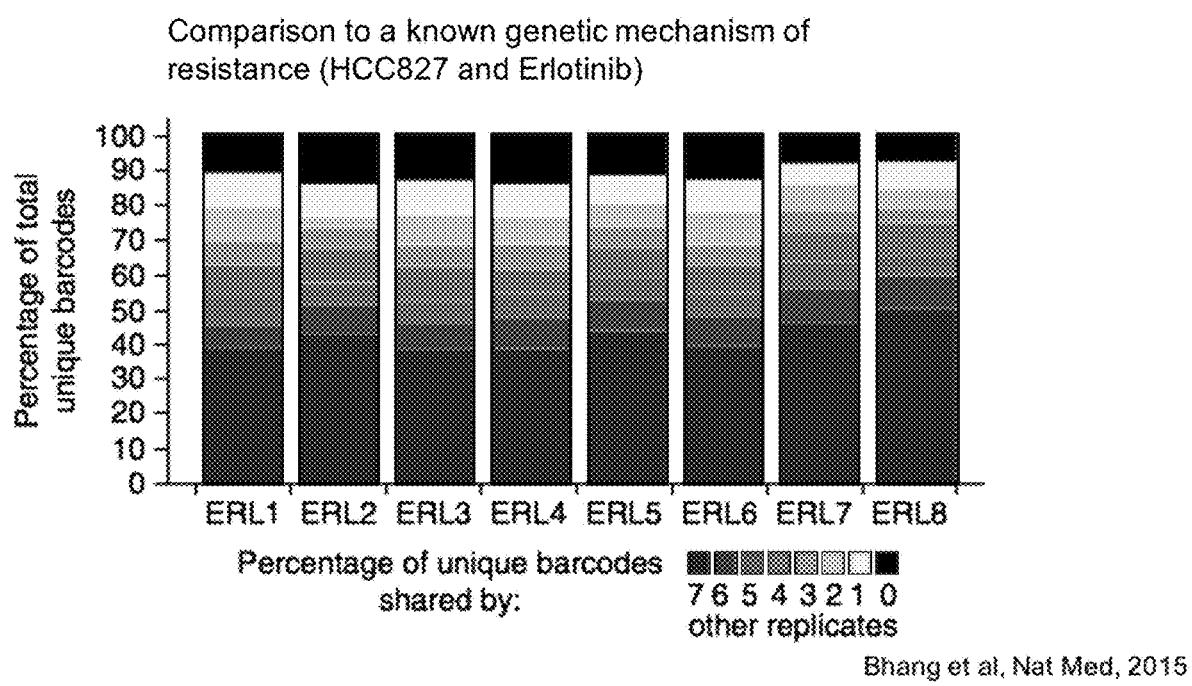
FIG. 5—Shows a comparison of barcoded cells to a known genetic mechanism of resistance (HCC827 and Erlotinib).
Figure 6:
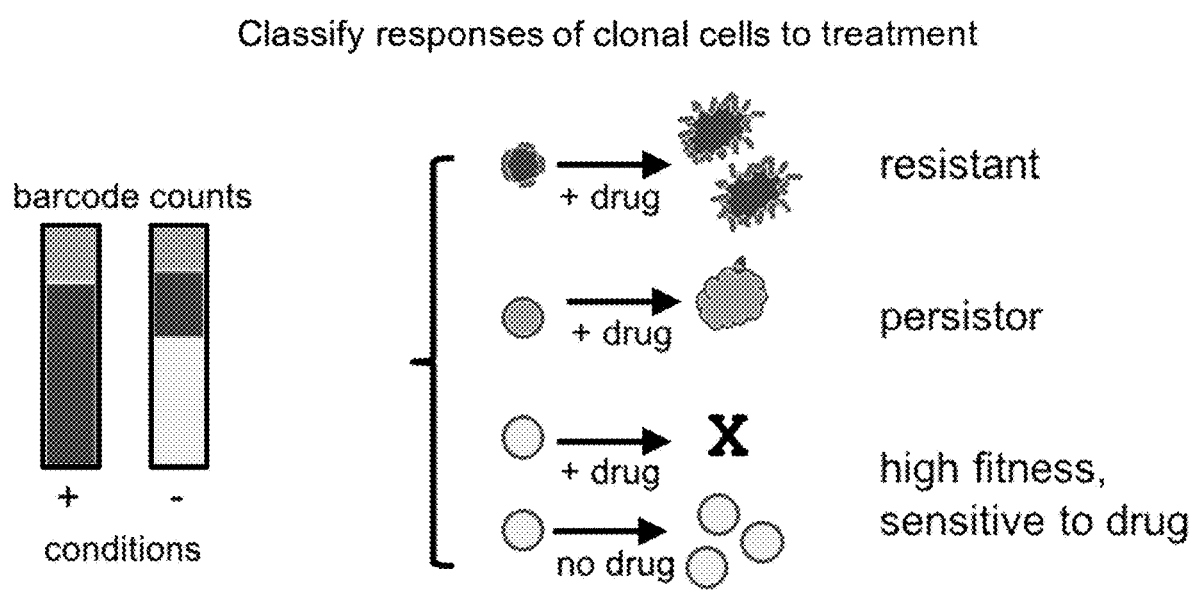
FIG. 6—Schematic showing selection of barcoded cells under drug+/−conditions.
Figure 7:
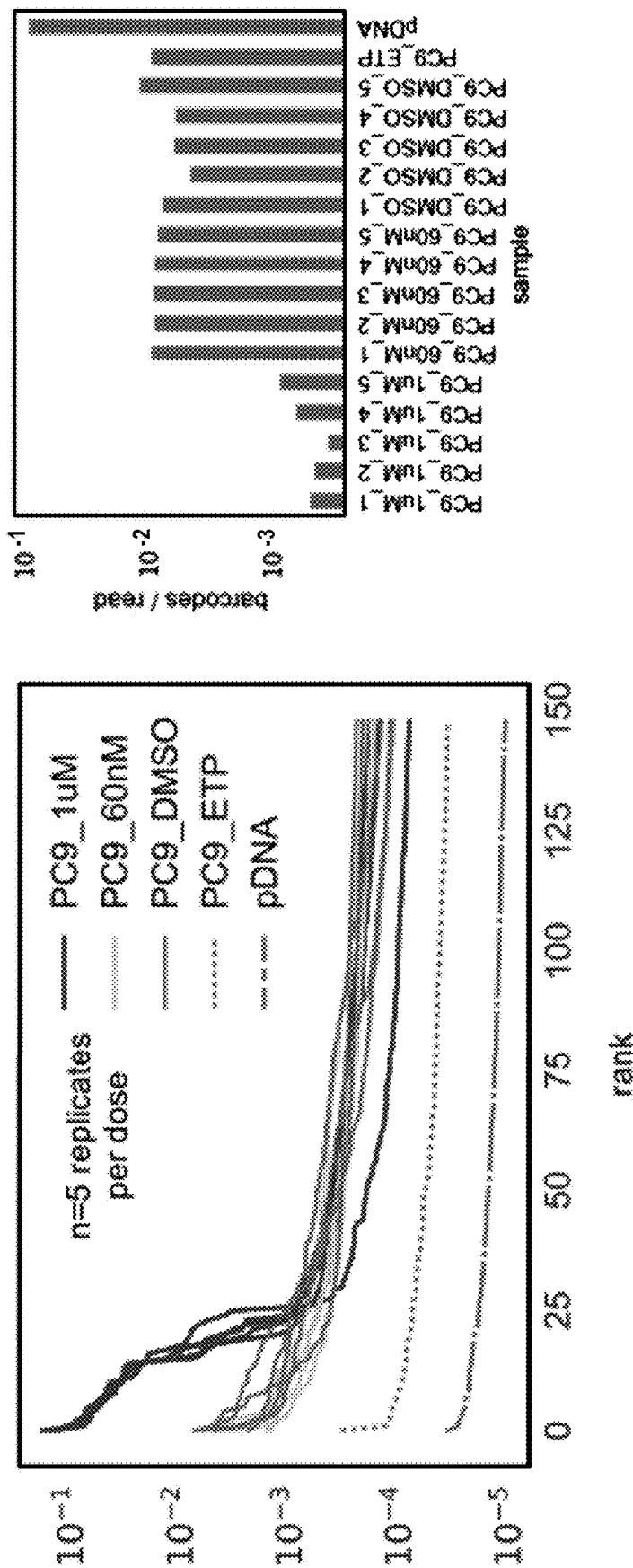
FIG. 7—Shows PC9 cells treated with different concentrations of erlotinib and the number of barcodes identified.
Figure 8:
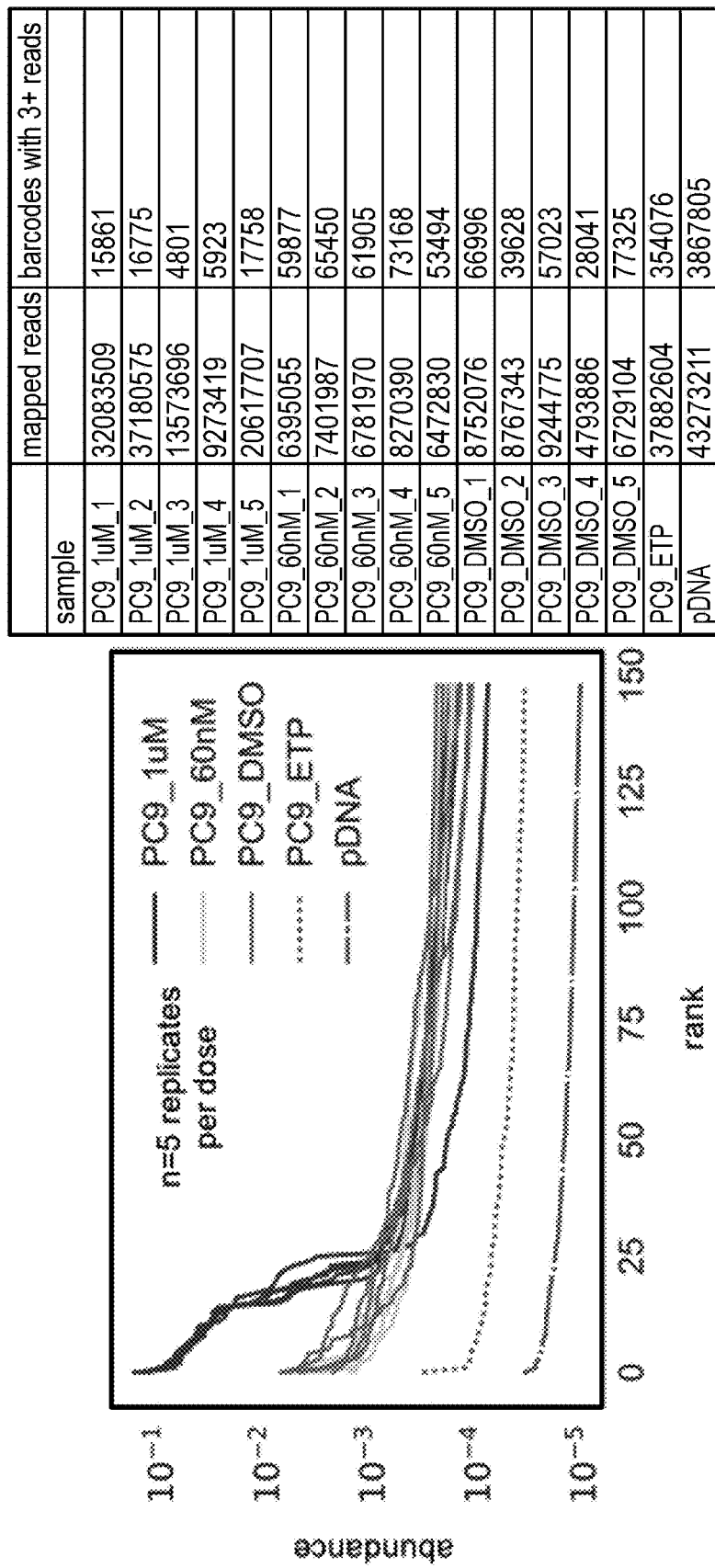
FIG. 8—Shows PC9 cells treated with different concentrations of erlotinib and the number of barcodes identified.
Figure 9:
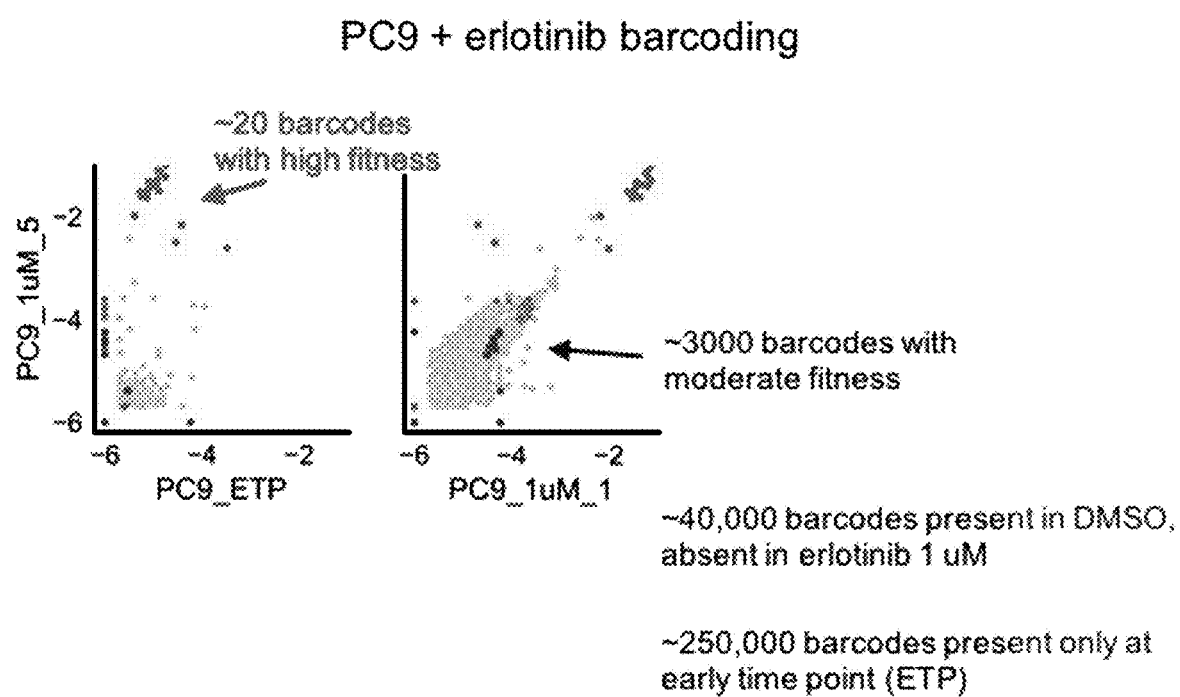
FIG. 9—Shows PC9 cells treated with erlotinib, including at an early time point (ETP), and a plot showing the number of barcodes identified.
Figure 10:
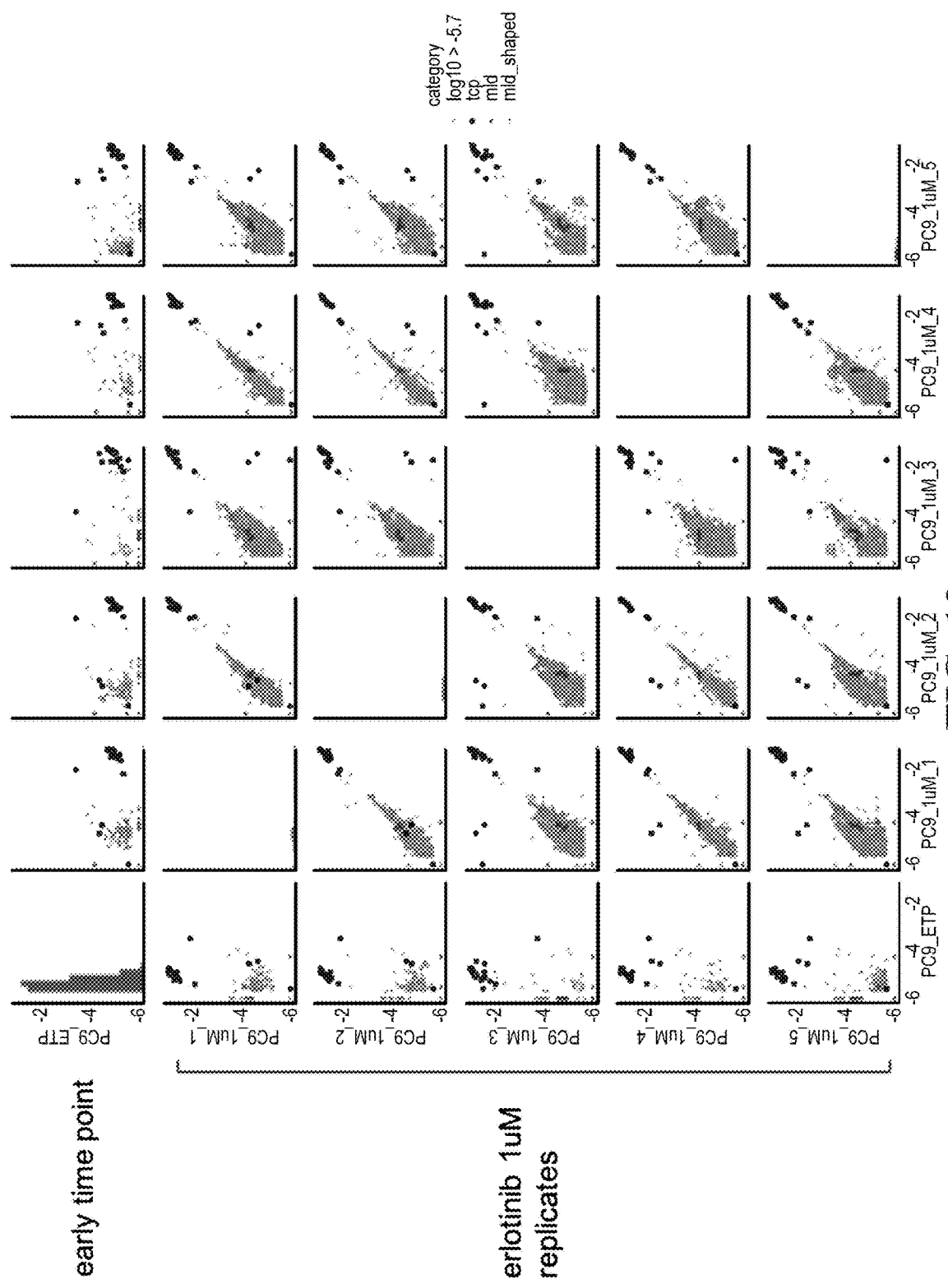
FIG. 10—Shows PC9 cells treated with erlotinib, including at an early time point (ETP), and plots showing the barcodes at 1 uM.
Figure 11:
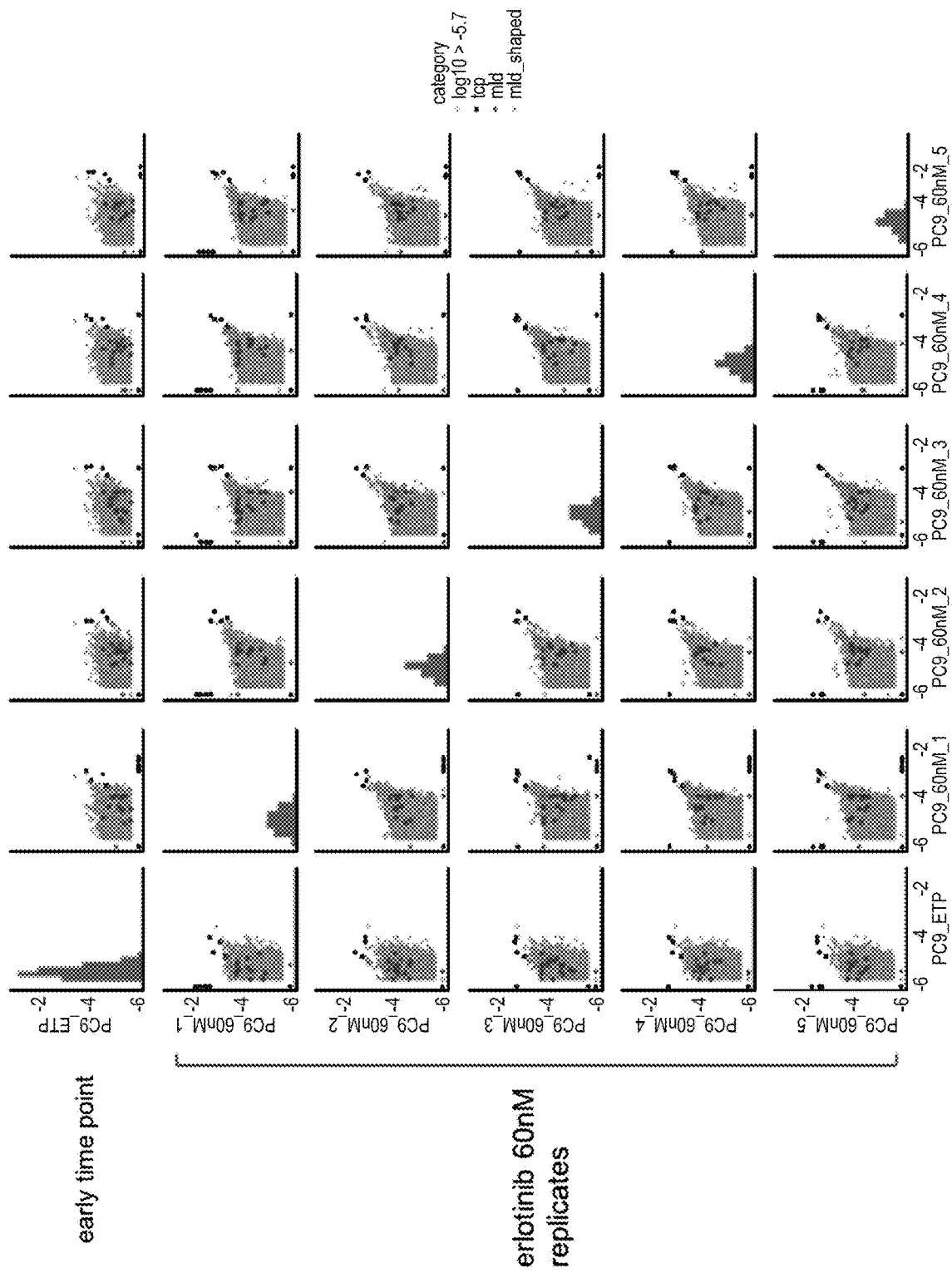
FIG. 11—Shows PC9 cells treated with erlotinib, including at an early time point (ETP), and plots showing the barcodes at 60 nM.
Figure 12:
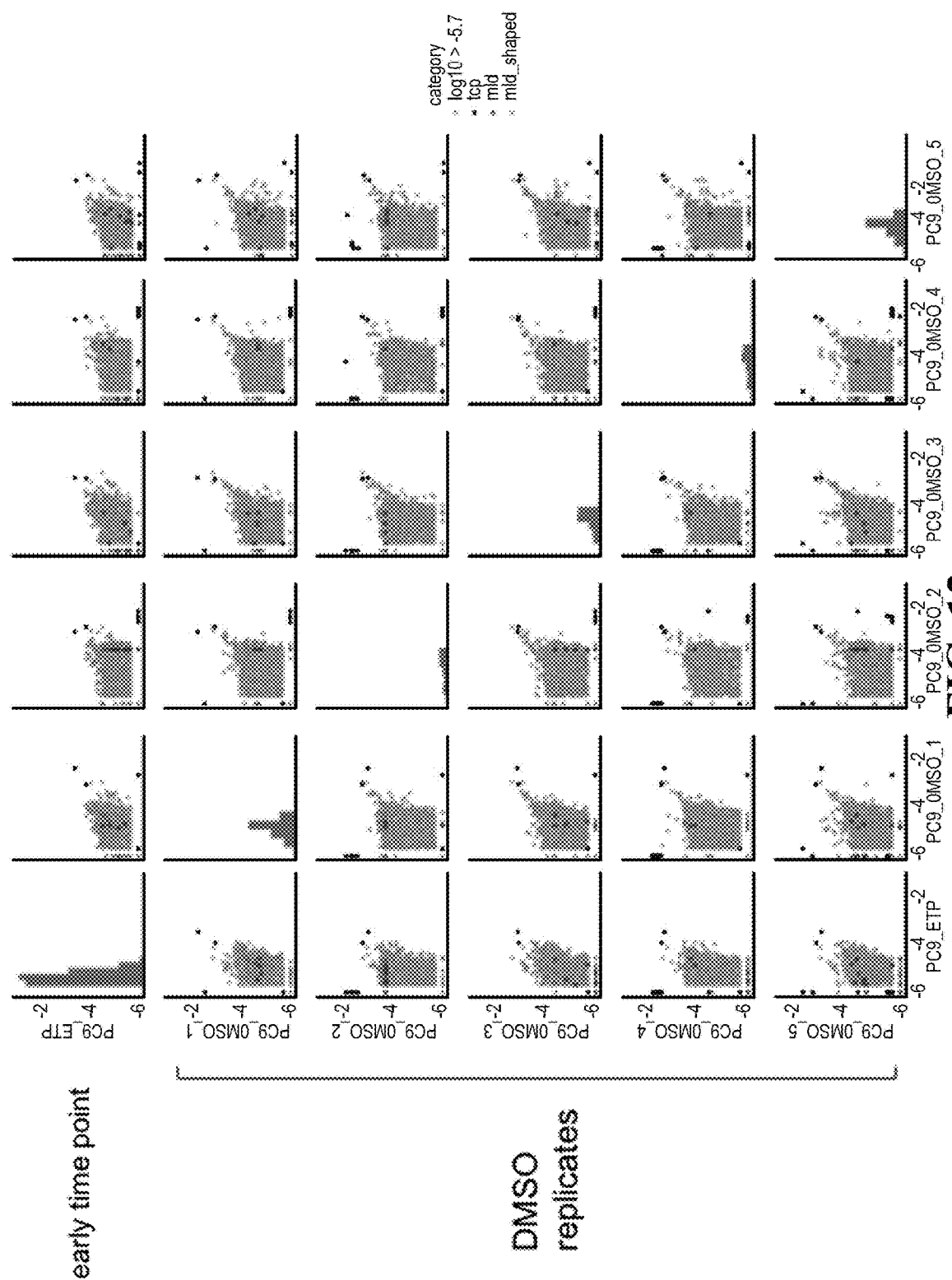
FIG. 12—Shows PC9 cells treated with DMSO, including at an early time point (ETP), and plots showing the barcodes.

Applicants and others (Bhang et al., Nature Medicine May 2015, Vol. 21:5, 440-448; and Nolan-Stevaux et al. 2013, PLoS ONE 8(6): e67316), have used inert DNA barcodes to track the evolution of populations of cells through targeted therapies. Bhang et al. demonstrated the presence of pre-existing resistant clones to EGFR inhibition in non-small cell lung cancer. Similarly, Applicants have observed that medulloblastoma cells exhibit predetermined, heritable and clonal resistance to BET-bromodomain inhibition (FIG. 4). However, it has been impossible to identify the phenotypic features of the clones destined to acquire resistance prior to or after drug treatment. This roadblock is the result of current barcoding technologies that do not allow the recovery of viable cells from specific lineages, which is essential to characterize phenotypic evolution of sub-lineages within a population. EvoSeq provides a solution for this challenge by facilitating the tracking and identification of individual populations of cells through treatment and allowing isolation of specific sub-clones from both pre- and post-treatment populations for phenotypic characterization. Specifically, EvoSeq has the capacity to:

a. Identify and characterize specific phenotypes that confer selection advantage.

b. Determine whether the identified resistance phenotypes were present in the pre-selection pool of cells, or whether they were induced by the selection pressure.

c. Elucidate the mechanism through which the resistant population exhibits altered regulation of resistance pathways. To achieve this one can, for example, profile the chromatin, RNA and DNA of specific barcode associated cells isolated from the pre- and post-treatment pools of cells.

d. Characterize the phenotypes of cells that exhibit the most sensitivity to treatment. Applicants can determine which barcodes are not present in resistant cells and can isolate these populations from the pre-treatment cells for phenotyping and characterization. EvoSeq allows for examining the phenotypes that contribute to negative selection.

Example 2—Demonstration of the Utility of EvoSeq

Resistance to EGFR-directed therapies in PC9 is frequently driven by second site mutations in EGFR (T790M). These mutations are presumed to be pre-existing prior to drug treatment and subsequently selected during drug treatment. This system provides a well-characterized model to directly determine if EGFRT790M resistance mutants that are selected for during treatment are present in the original, untreated populations. Applicants introduced barcoded libraries into PC9, immediately expanded and cryopreserved a fraction of the parental population and exposed the remaining population (in replicates) to Erlotinib. Applicants also cryopreserved a fraction of cells one week after initiation of treatment. Barcode deconvolution of the parental and evolved population identified drug-resistant subpopulations. Directed sequencing of the parental and evolved population was used to confirm that T790M predominates and is correlated with barcode enrichment, thus identifying barcodes that mark cells containing T790M mutations. A subset of the cells predicted to contain the T790M mutation can be isolated and sequenced from both the parental and evolved population. Applicants demonstrated the ability of EvoSeq to capture pre-existing and evolved resistant lineages by assessing their sensitivity to Erlotinib. Applicants validated the capacity to uncover driver genomic alterations by directed sequencing of EGFR in recovered lineages. Finally, Applicants highlighted the capacity of EvoSeq to function as a molecular time-machine by profiling the transcriptome of the same lineage of cells at different evolutionary timepoints by performing RNA-sequencing of cells from the same lineage retrieved from populations of cells that have been cryopreserved at different points in treatment.

Example 3—Demonstration of the Utility of EvoSeq

The barcoding library identifies lineages with distinct profiles of resistance within a population across several, i.e., more than one cell line (e.g., PC9 and medulloblastoma). Evoseq can include:
1. Pairwise correlation (averaging replicates, normalizing ETP)
2. Breakdown of barcodes across replicates
3. Lineage expansion plots—to show visually where the bottleneck takes place (and when it takes place) and how severe the bottleneck is (what comes out the other end)
4. Repeat barcode experiment with all the major EGFR inhibitors to see if can wipe it out (clustering barcodes by relative fitness in the different treatments).

Retrieved populations recapitulate resistant lineage (or the delta fitness/phenotype of the expected population)—e.g., the difference of IC50 from parental population/resistance. Evoseq can include measuring:

5. IC50s
6. Growth in drug
7. Spike in to another barcode experiment
8. new generation EGFR inhibitors Genetic/functional characteristics explain differences between mode of resistance/resistance profile etc. within the retrieved population. Evoseq can also include measuring:

9. genomics
10. Chromatin state

Example 4—Retrieval Reporter is Highly Specific

Activation of the reporter with the matching guide produces plus one frame indels (FACs mCherry positive cells) compared to 0% for mismatched guide controls.

Applicants further tested specificity by targeting spiked in barcodes. Applicants dilute the barcodes to different concentrations and recover cells.

To improve the sensitivity of the system, Applicants designed a second reporter construct that captured both edited frames (the two edited frames). This modification resulted in an increased sensitivity and maintained a high specificity.

Including a second reporter gene (e.g., antibody) would allow Applicants to preselect populations.

Example 5—Labeling Cells with sgRNA Barcodes Allows for Tracking of Populations of Cells Through Treatments Applicants first tested the ability to retrieve cells engineered to exhibit resistance to treatment with hygromycin. Applicants generated populations of TetRcas9-HeLa cells in which hygromycin resistance cells were spiked in. Applicants infected cells with the library (low MOI) and allowed the cells to expand. Sequencing of the early time point (ETP) revealed library uniformity of distribution of barcodes (range in abundance or variance of barcode abundance). Cells were passaged in hygromycin (or vehicle control) in replicate experiments. Applicants identified barcodes shared among replicates. Applicants hypothesized that these barcodes identify cells that harboured the hygromycin resistance cassette.

Applicants designed frameshift reporters with the capability to retrieve cells that harbored these specific barcodes from the pretreatment pool that spanned this level of fitness. Applicants isolated these cells.

Applicants next tested the ability of the system to retrieve cells that spontaneously exhibit resistance and dissect functional modes of resistance in a well-defined cancer model. PC9 cells have been previously shown to harbor predetermine resistance mutations. Applicants barcoded a population of cells (with a low MOI) and selected using 2 doses of Erlotinib (60 nM and 1 uM) across replicates.

Figure 13:
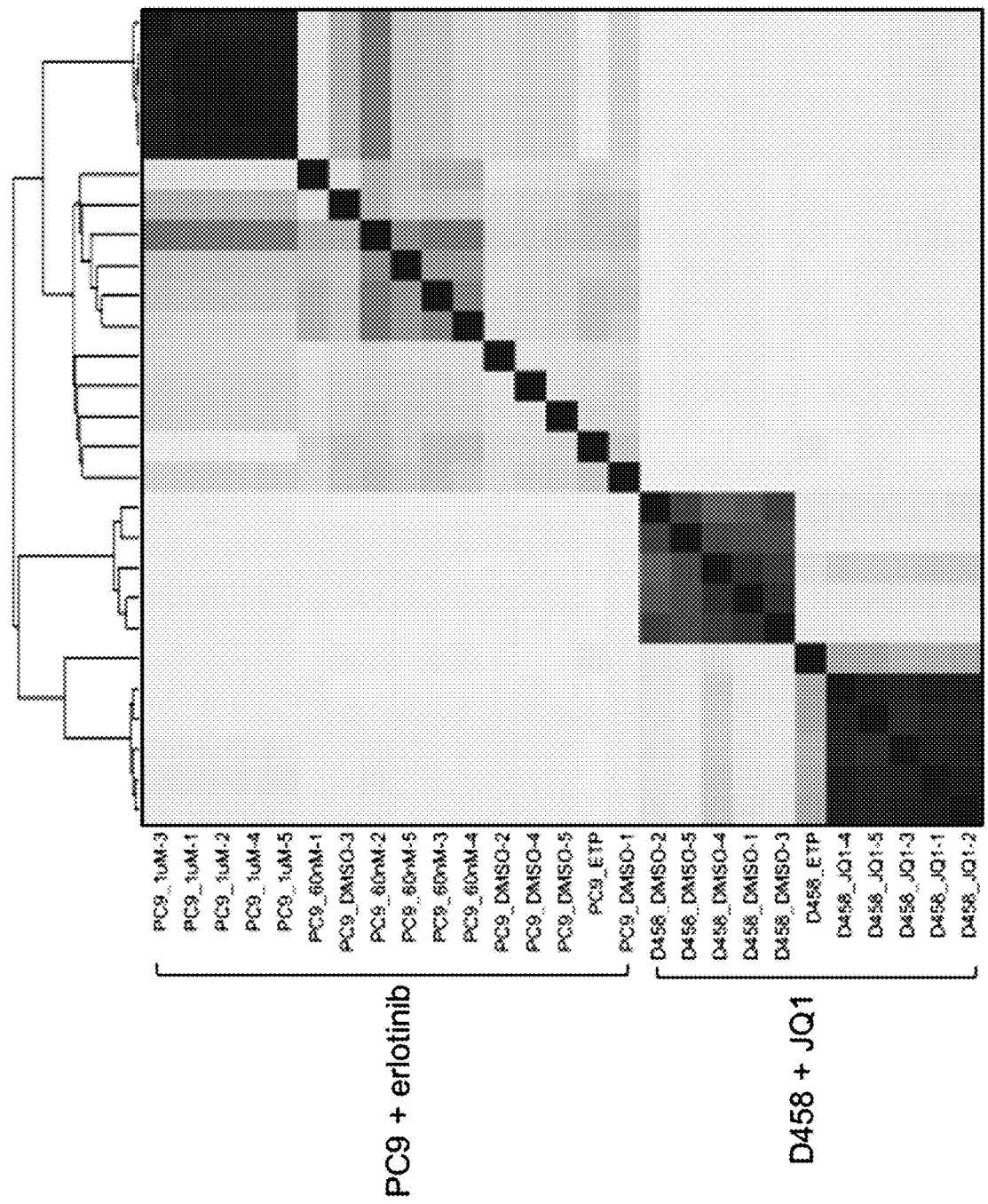
FIG. 13—Plot showing that barcoded cells from different conditions cluster together.

Deep sequencing of the ETP retrieved the number of barcodes. Barcodes for the two concentrations were detected in the post treatment samples. Applicants observed significant correlation of barcode distributions between replicates passaged under the same conditions (DMSO, 60 nM or 1 uM, FIG. 13). Applicants identified barcodes shared among replicates. These findings suggest that there is a heritable, predetermined resistance mechanism in PC9 cells. (see Figures).

Example 6—Construct Design for Retrieval

The basic concept is to use the high specificity of Cas9 and create a reporter with an indel with as small as possible window to generate the effect. 60 bp window to turn on GFP. For both GFP and selection marker to be in frame the construct requires two indels, one in the small window from GFP and another in the ~50 bp small window in front of the other selection (e.g. hygro, mCherry). The construct requires both to get both genes in frame.

Applicants noticed low background and low sensitivity and further reduced the background rate by removing upstream ORFs, removing any start codons upstream of the reporter (and some within construct) and included a translational stop sequence immediately before the start Kozak (three in all three frames) to prevent translation from a possible upstream site. That change resulted in about 3% activation and no activated cells in one million background cells (FACS). To improve sensitivity Applicants switched to a stronger promoter and achieved an approximately 2.5-fold increase in sensitivity. As described herein different types of selection markers may be used. Additionally, all of the reporter genes were codon reoptimized to remove start and stop codons in all three frames and in some cases methionine (ATG) sequences were mutated to leucine to prevent possible start codons in the in-frame sequences.

Limitations of EvoSeq include random integration. Applicants did not observe any signal in the DMSO controls in any of the experiments to suggest a survival advantage.

Example 7—Lineage Barcode-Specific Reporter and Retrieval

Figure 14:
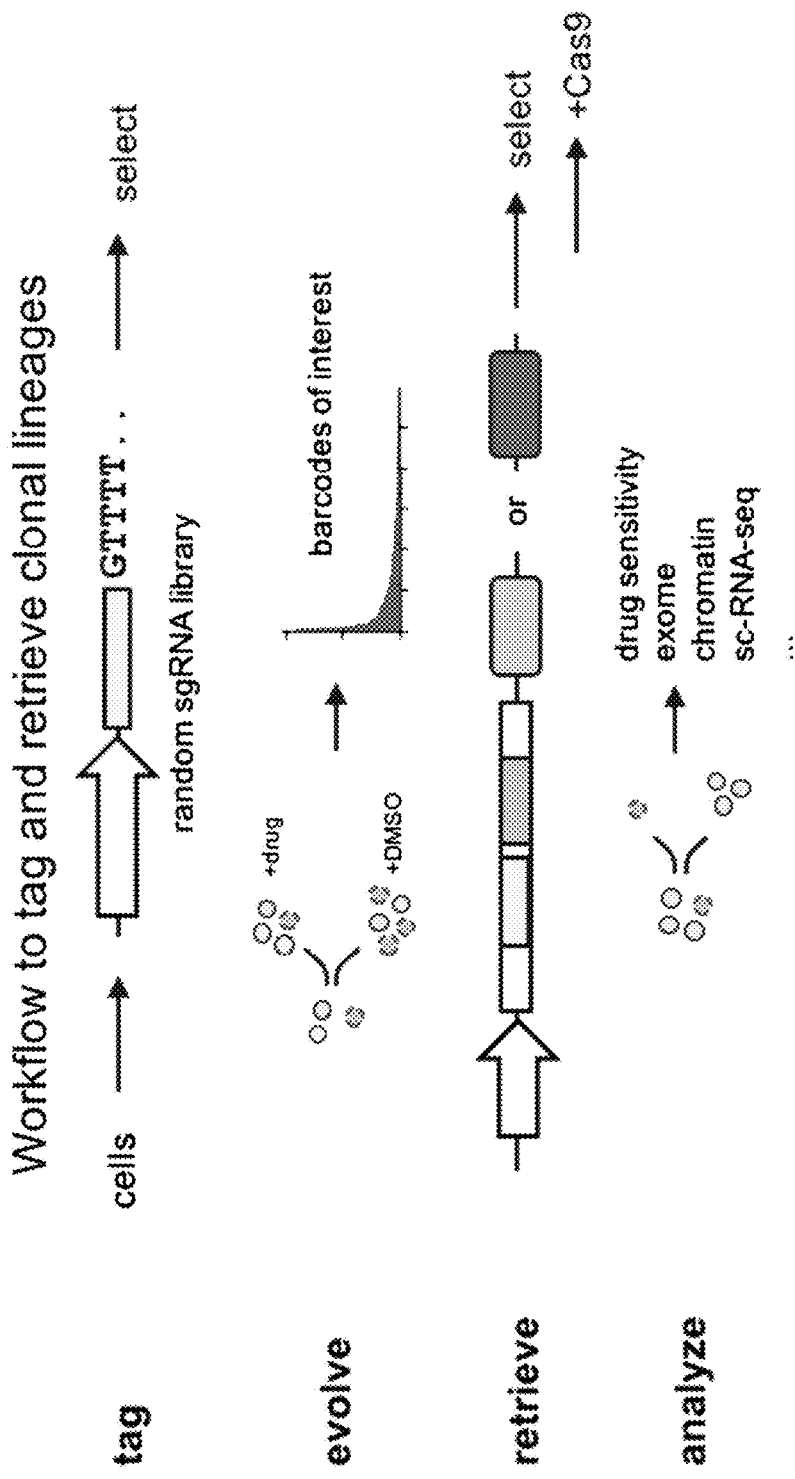
FIG. 14—Shows an example workflow to tag and retrieve clonal lineages.
Figure 15:
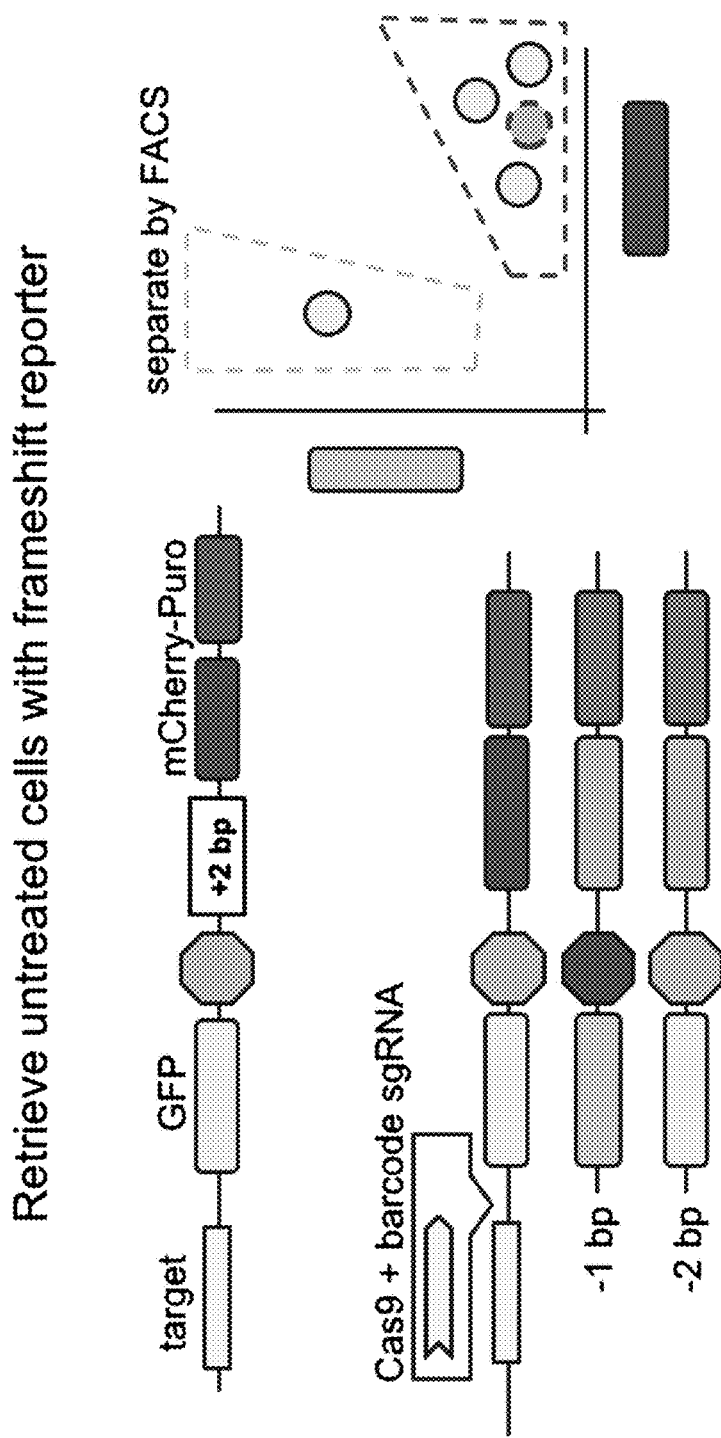
FIG. 15—Shows an example of retrieval of cells with a frameshift reporter.
Figure 16:
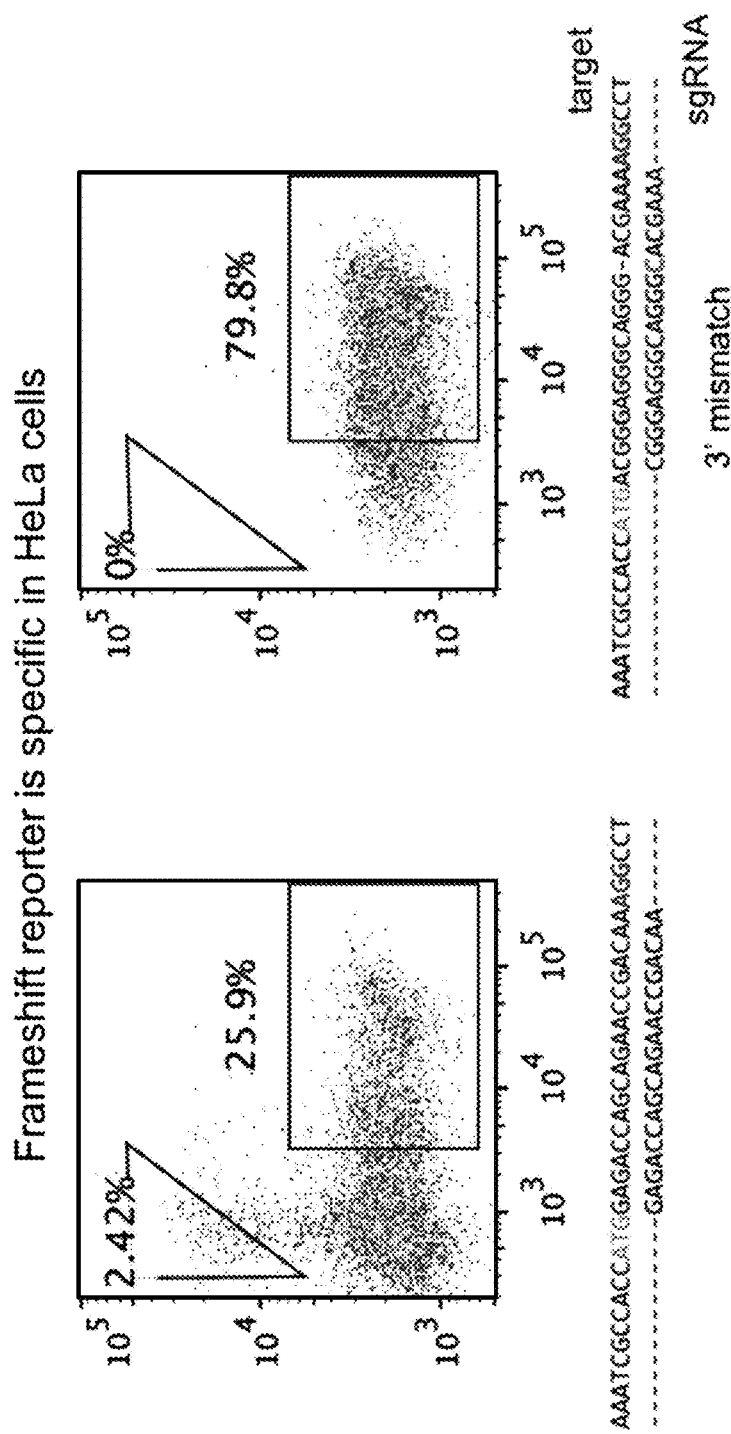
FIG. 16—Shows that the frameshift reporter is specific for the targeting guide sequence of interest in HeLa cells. Cells are recovered when the guide sequence has no mismatches, but cells are not recovered when a single 3' mismatch is introduced (SEQ ID NOs. 1-4).
Figure 17:
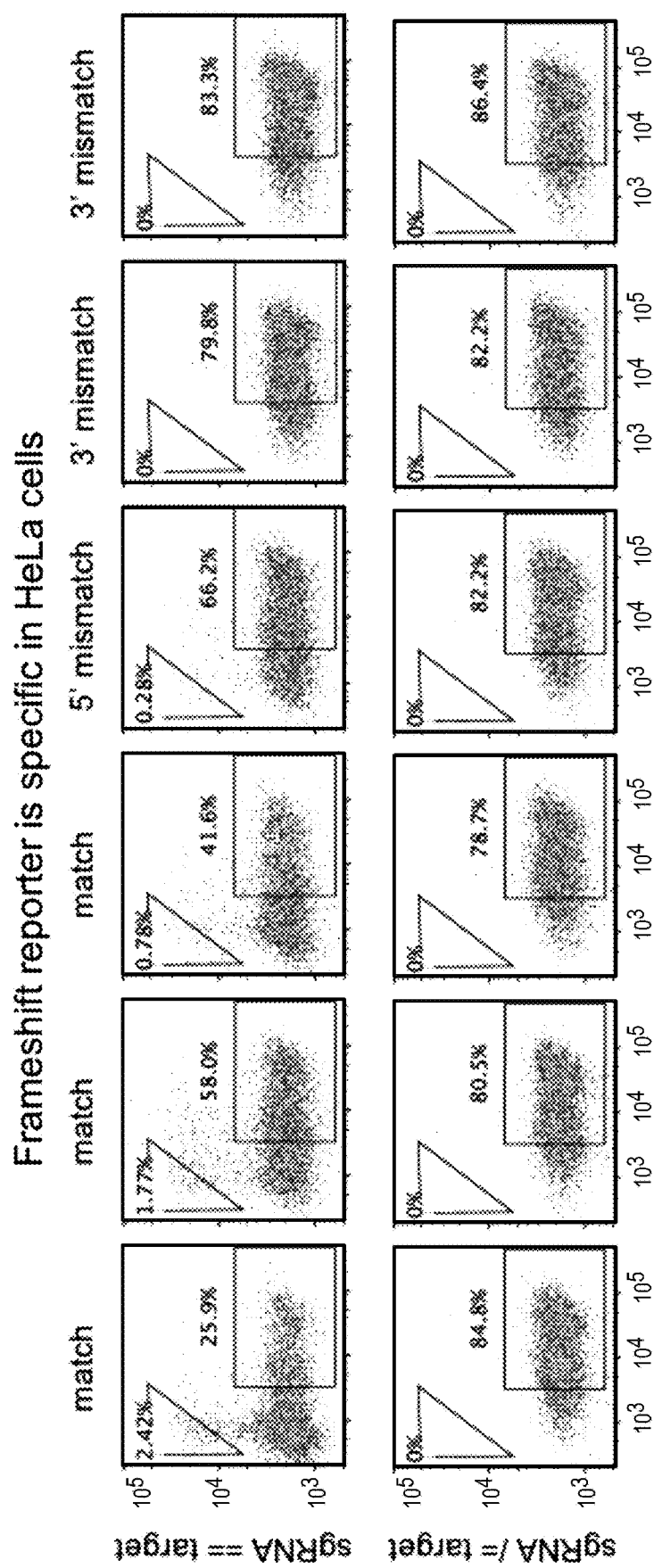
FIG. 17—Shows that the frameshift reporter is specific for the targeting guide sequence of interest in HeLa cells.
Figure 18:
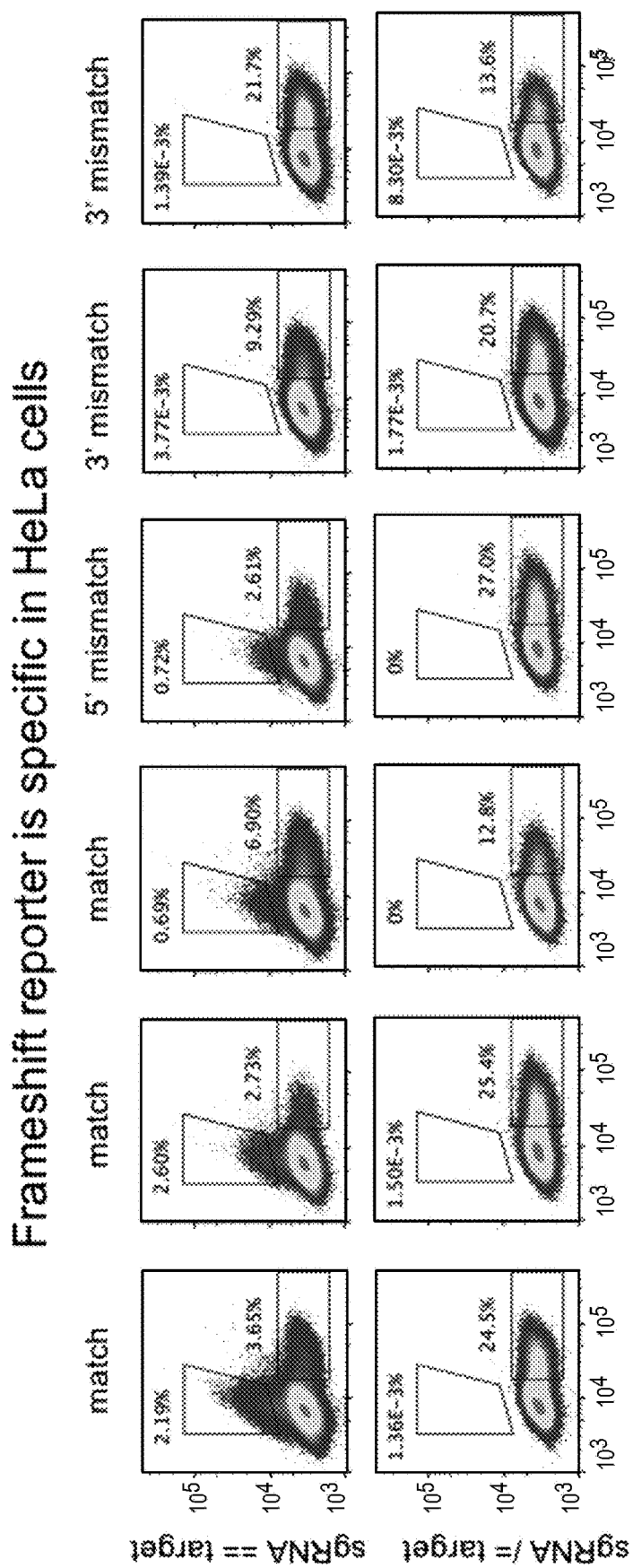
FIG. 18—Shows that the frameshift reporter is specific for the targeting guide sequence of interest in HeLa cells.
Figure 19:
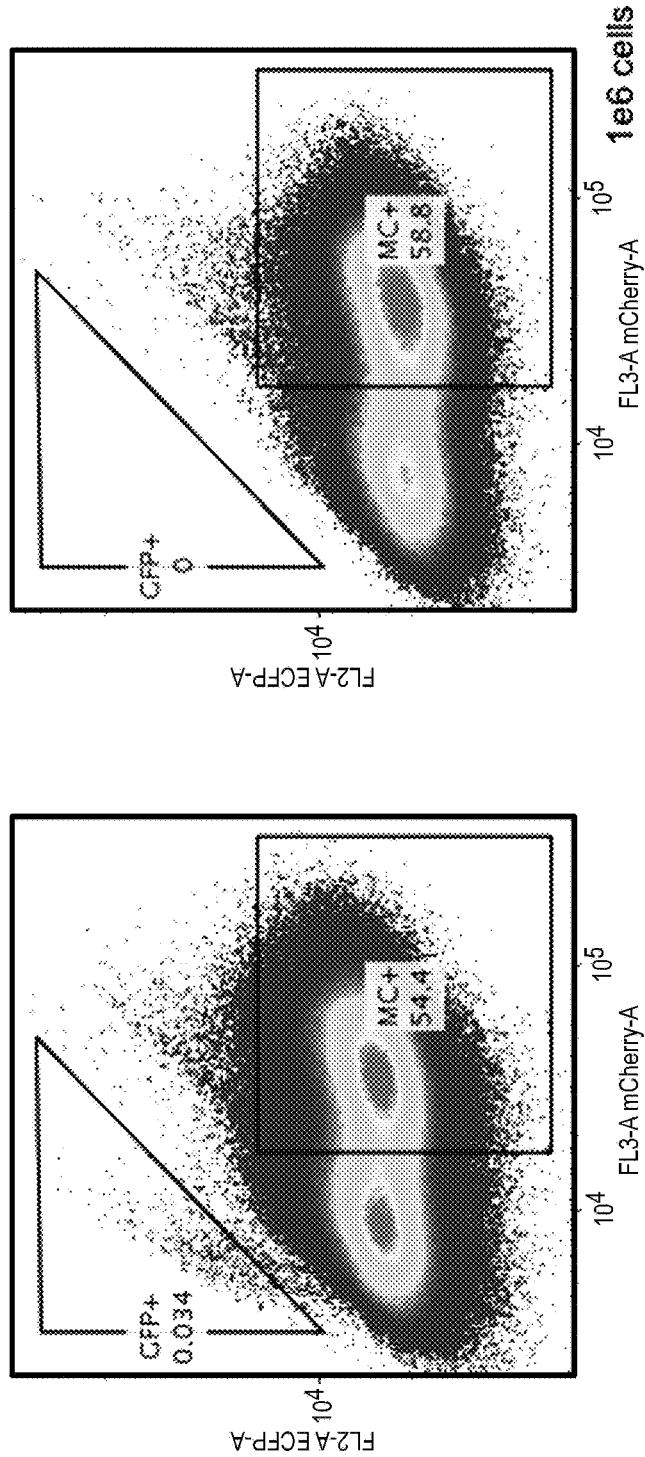
FIG. 19—Shows that the frameshift reporter is highly specific in HeLa cells.
Figure 20:
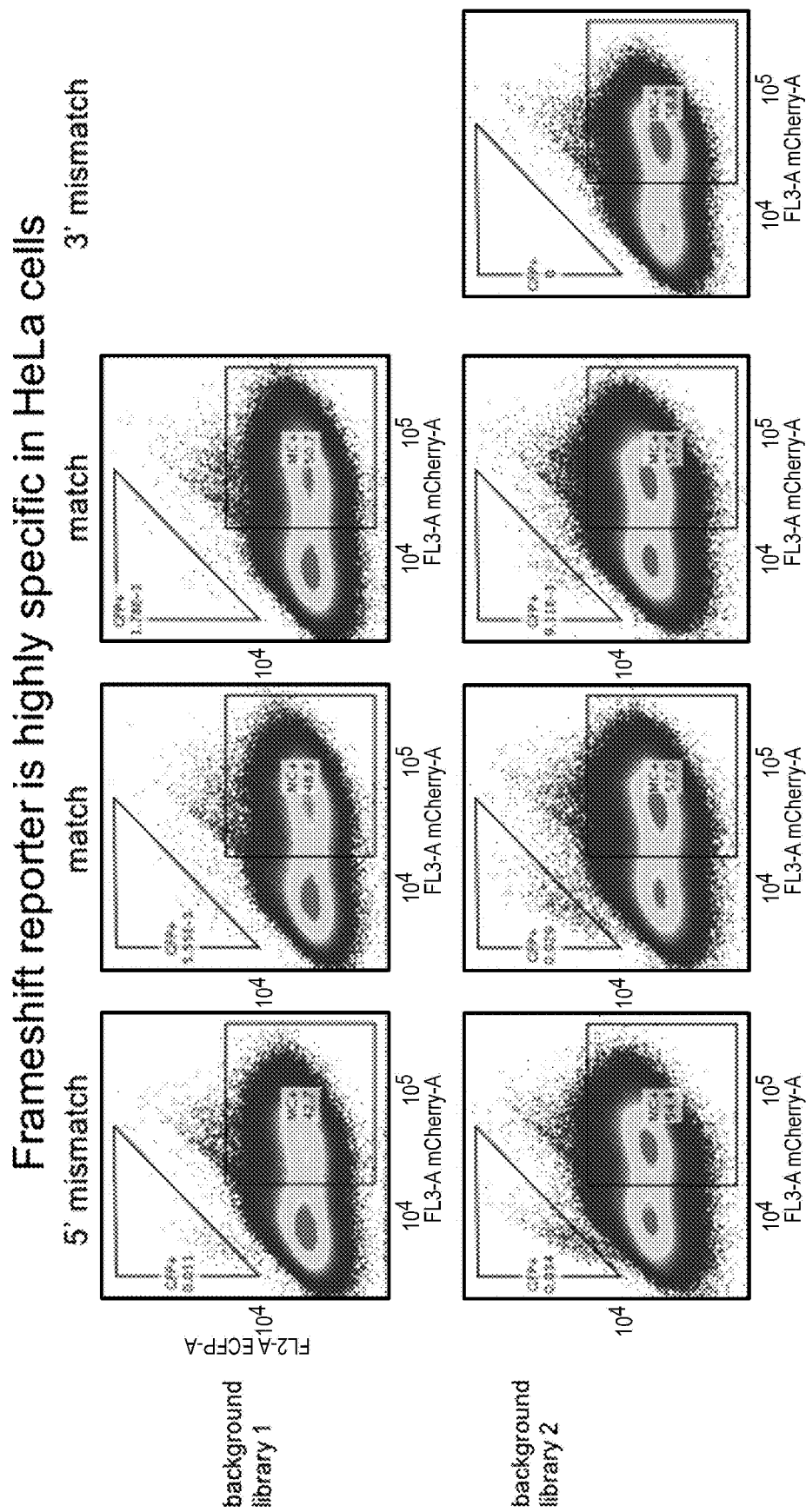
FIG. 20—Shows that the frameshift reporter is highly specific in HeLa cells using background libraries.
Figure 21:
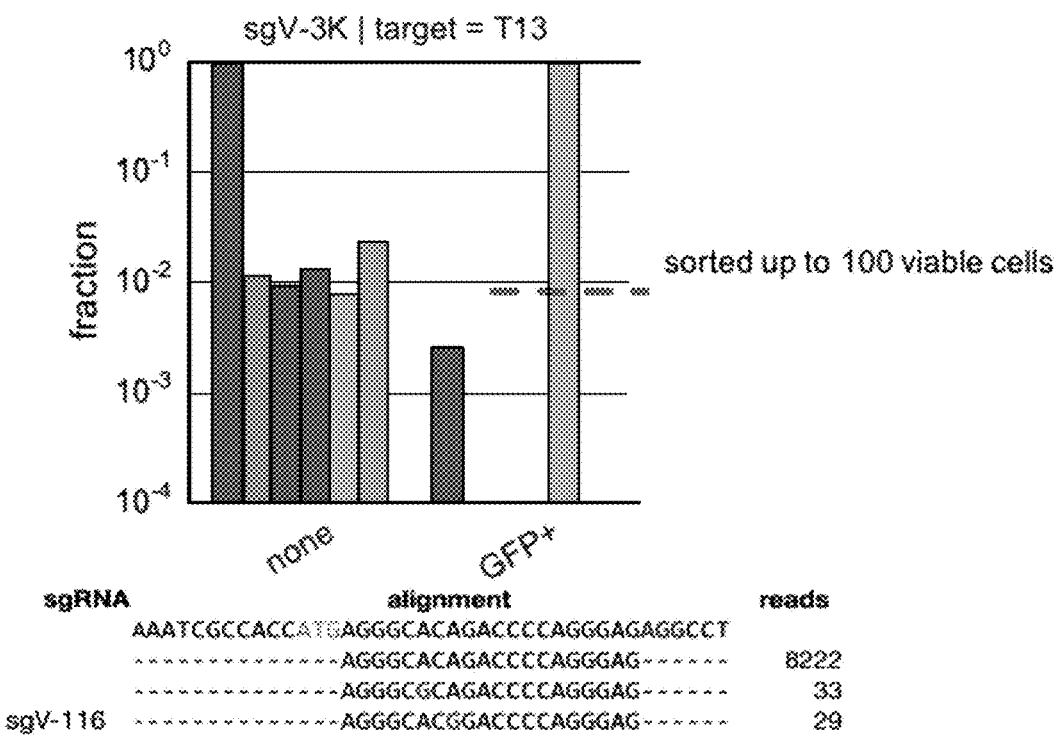
FIG. 21—Shows that reporter constructs that are activated by guide sequence barcodes in specific cells can be used to separate the cells by FACS and the targeted sequences can be verified by next generation sequencing (SEQ ID NOs. 5-8).
Figure 22:
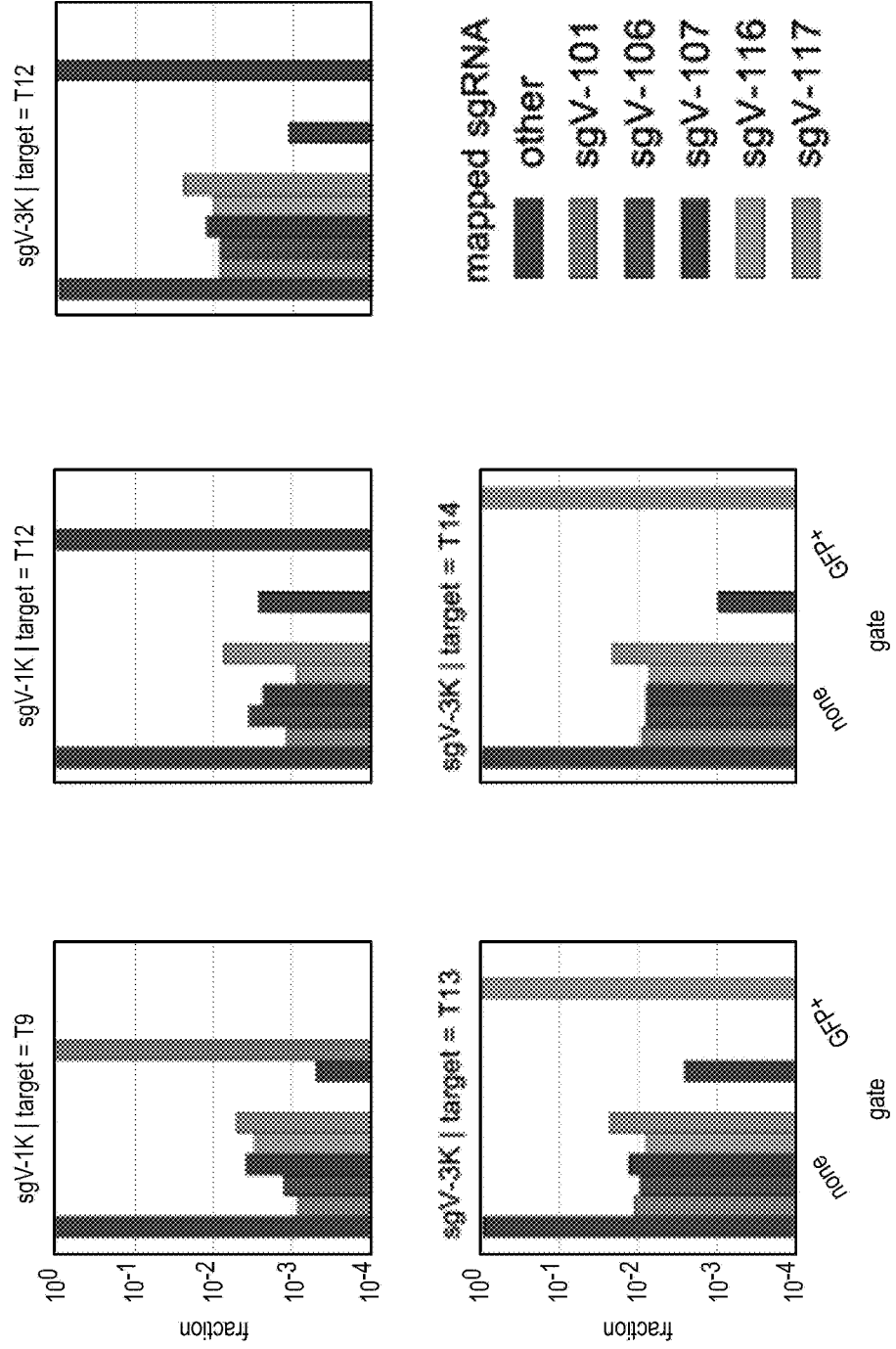
FIG. 22—Shows that reporter constructs that are activated by guide sequence barcodes in specific cells can be used to separate the cells by FACS. The cells can be cultured and the targeted sequences can be verified by next generation sequencing.
Figure 23:
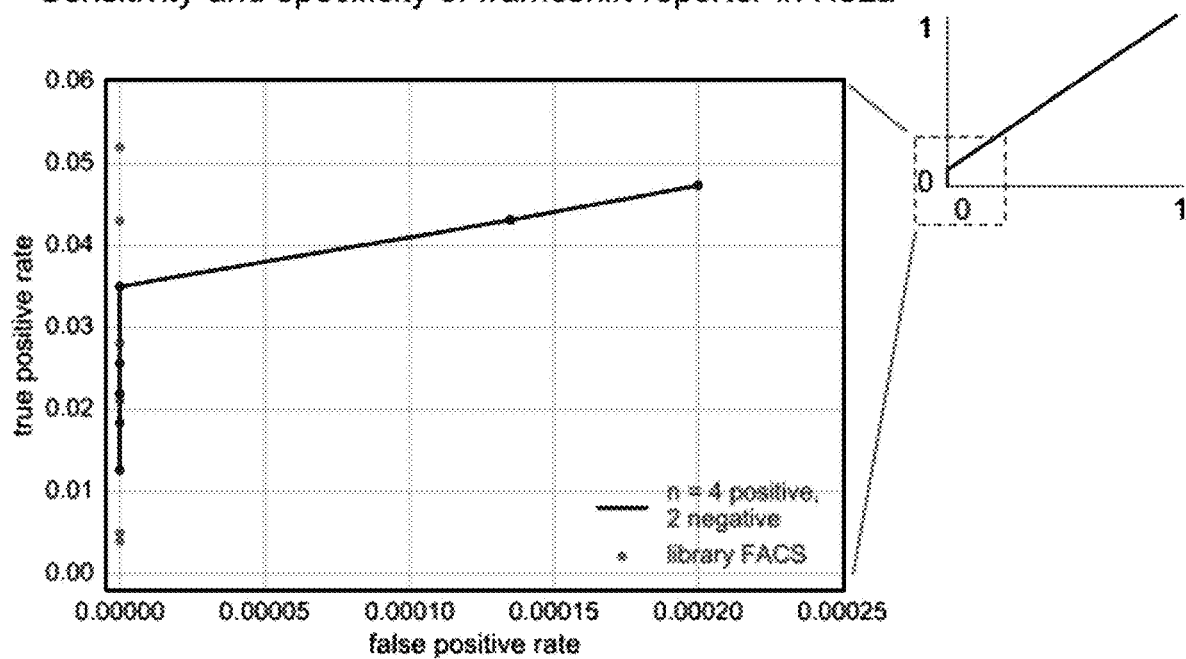
FIG. 23—Shows the sensitivity and specificity of the frameshift reporter in HeLa cells.
Figure 24:
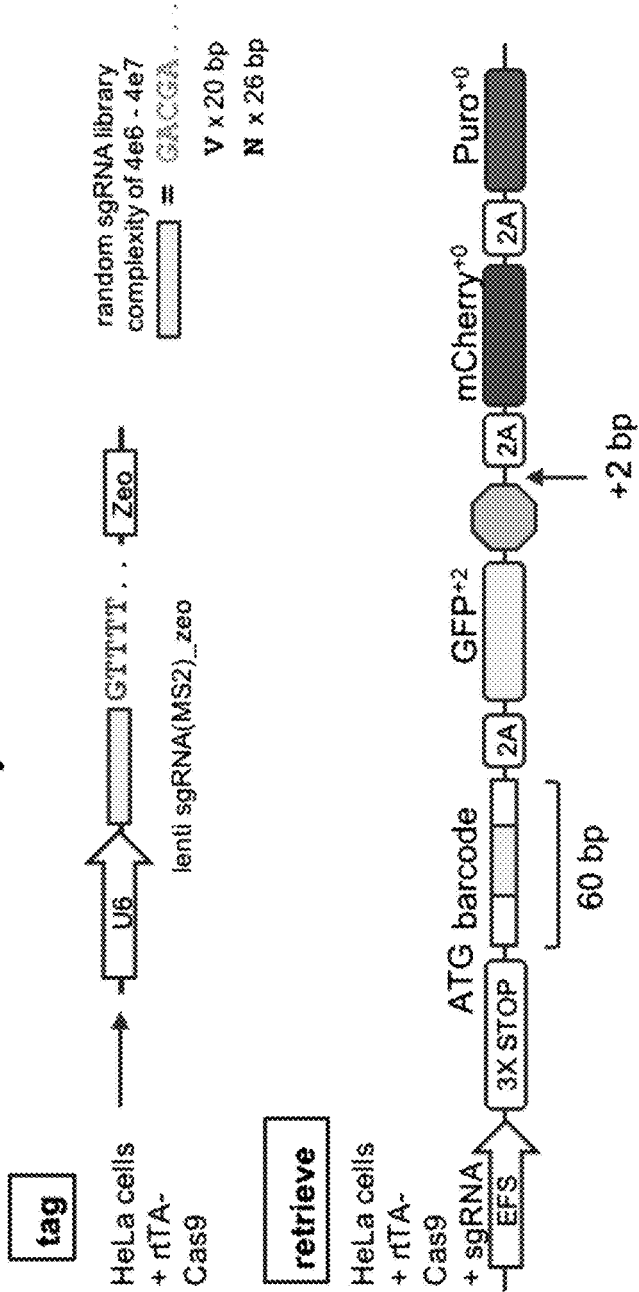
FIG. 24—Shows a tagging construct containing the guide sequence barcode and selectable marker and shows a retrieval construct.
Figure 25:
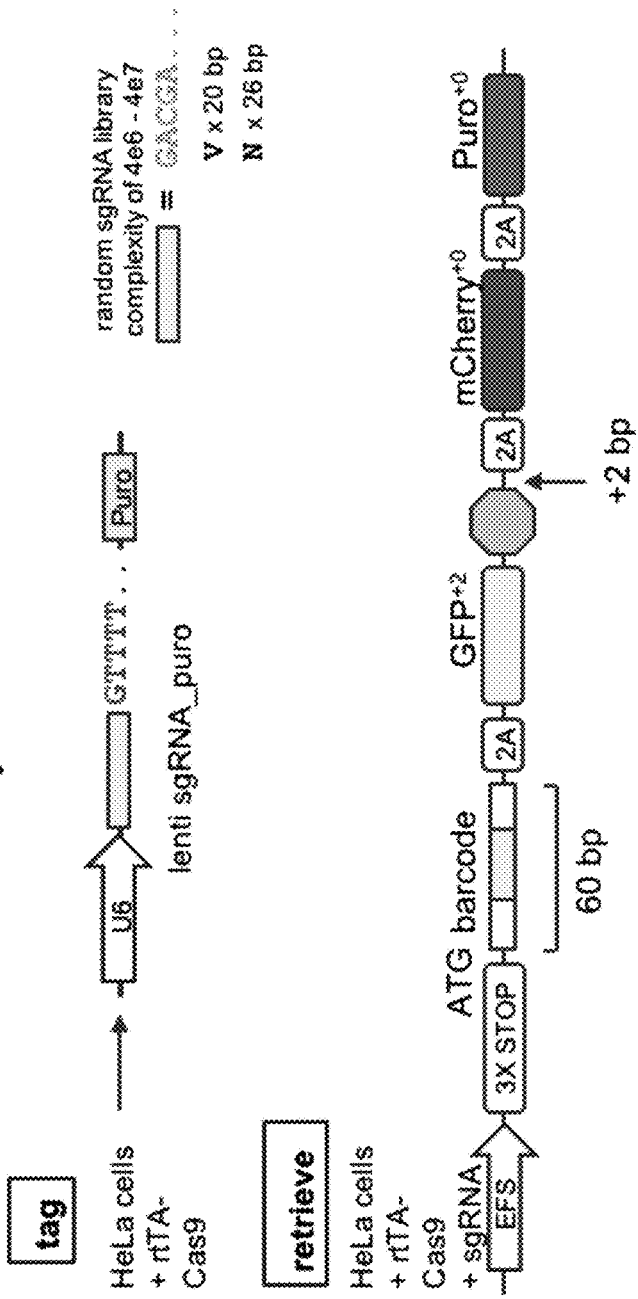
FIG. 25—Shows a tagging construct containing the guide sequence barcode and selectable marker and shows a retrieval construct.
Figure 26:
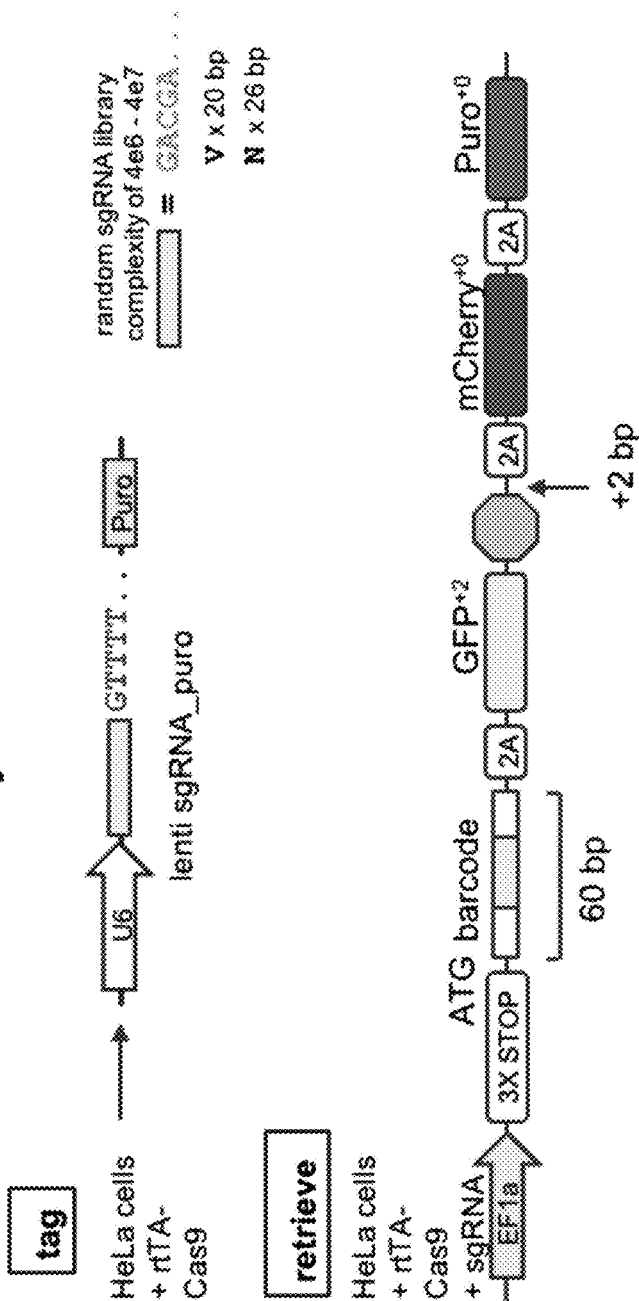
FIG. 26—Shows a tagging construct containing the guide sequence barcode and selectable marker and shows a retrieval construct.
Figure 27:
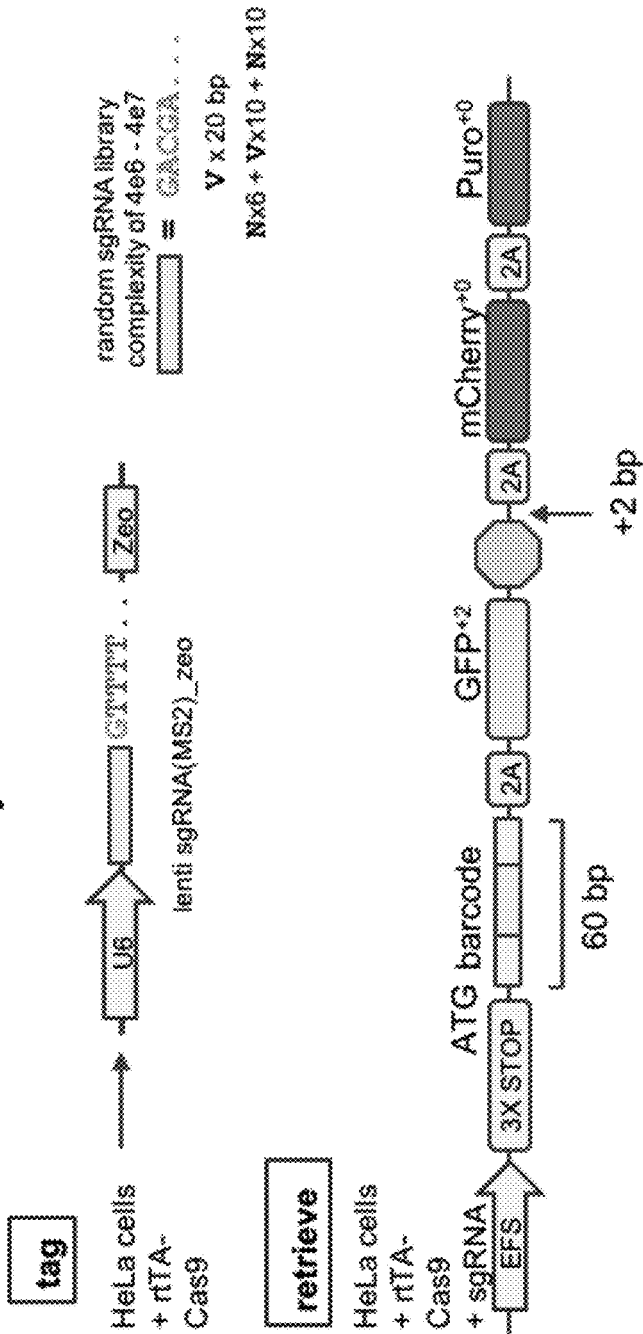
FIG. 27—Shows a tagging construct containing the guide sequence barcode and selectable marker and shows a retrieval construct.
Figure 28:
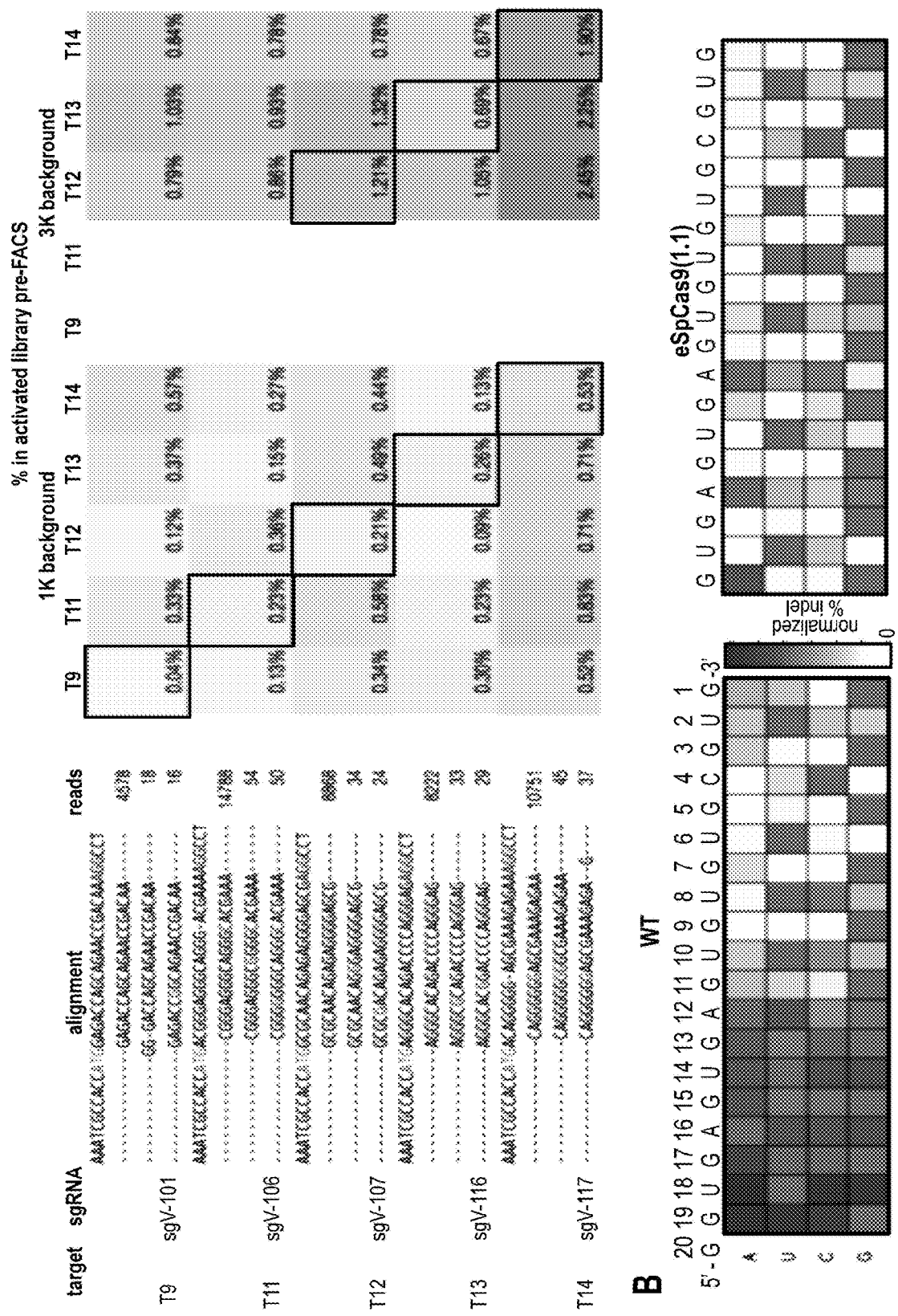
FIG. 28—Shows the specificity of obtaining the targeted guide sequence barcode and the system can use eSpCas9 (1.1) to improve indel formation (SEQ ID NOs. 9-28).
Figure 29:
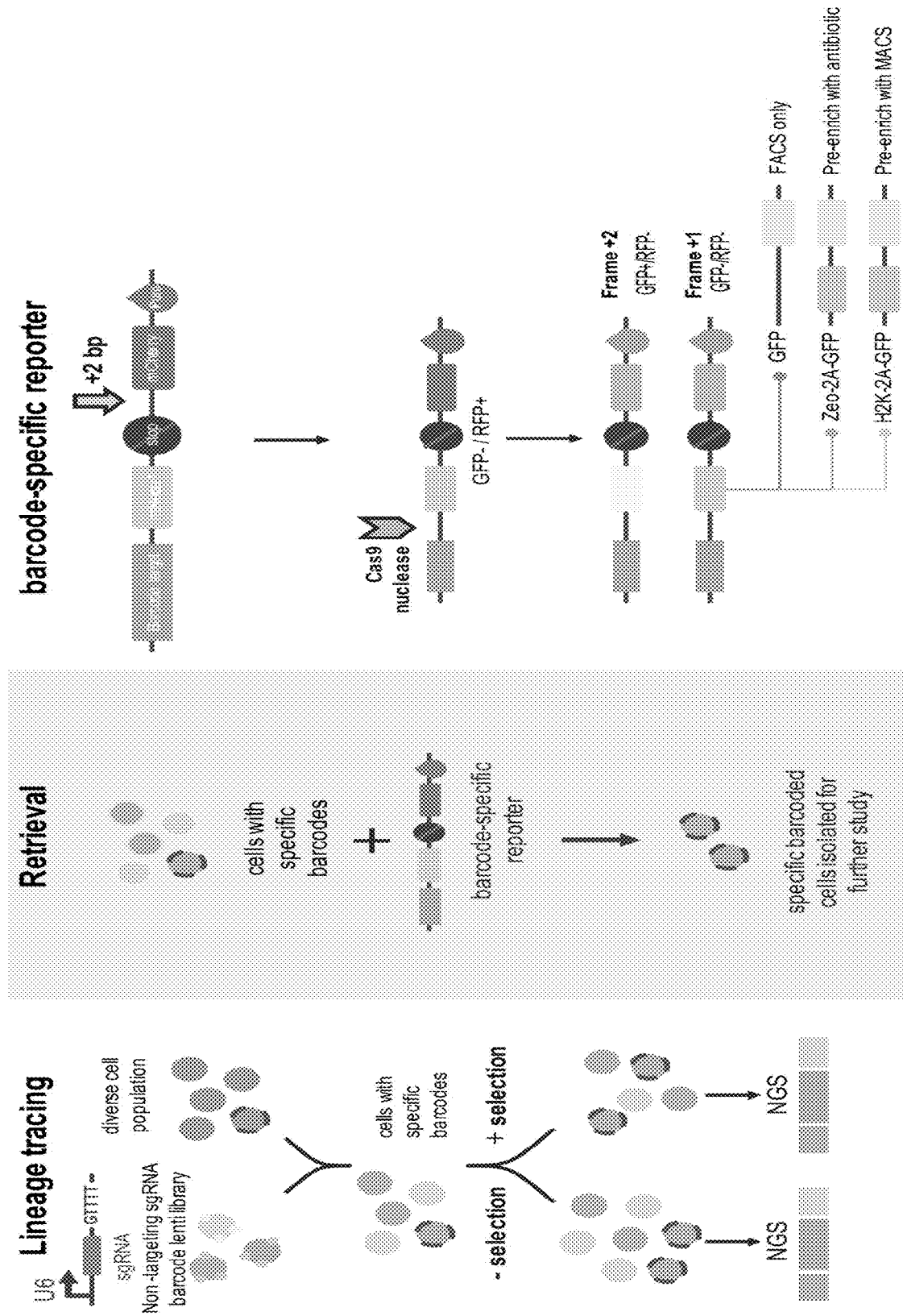
FIG. 29—Shows schematics for lineage tracing using a non-targeting sgRNA barcoding library (left), retrieval of cells with specific barcodes (center), and barcode specific frameshift reporters (right).
Figure 30:
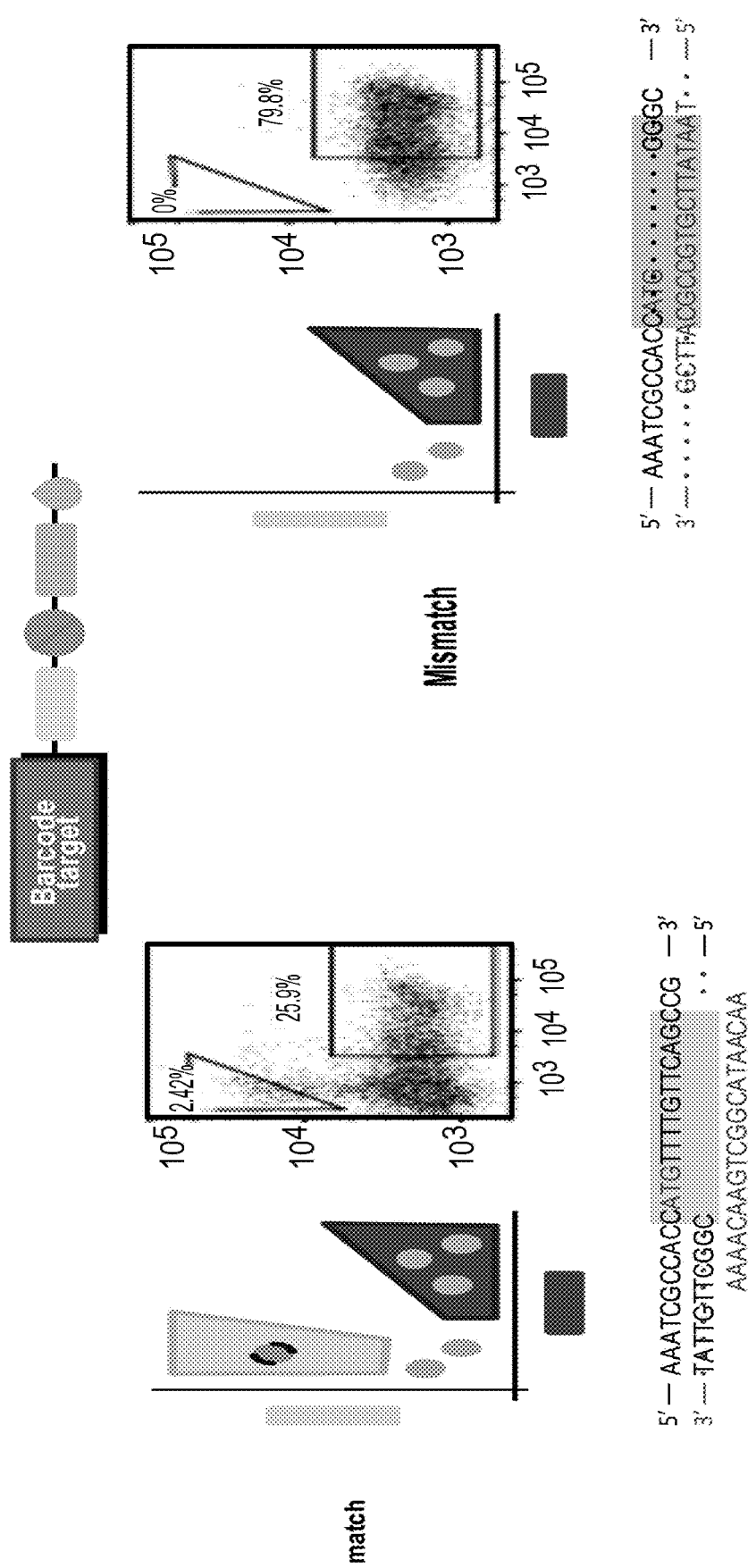
FIG. 30—Shows a schematic of Cas9-mediated, sgRNA-barcode-specific GFP activation and results of FACS retrieval with a matching barcode target and a mismatching barcode target (SEQ ID NO:29-33).
Figure 31:
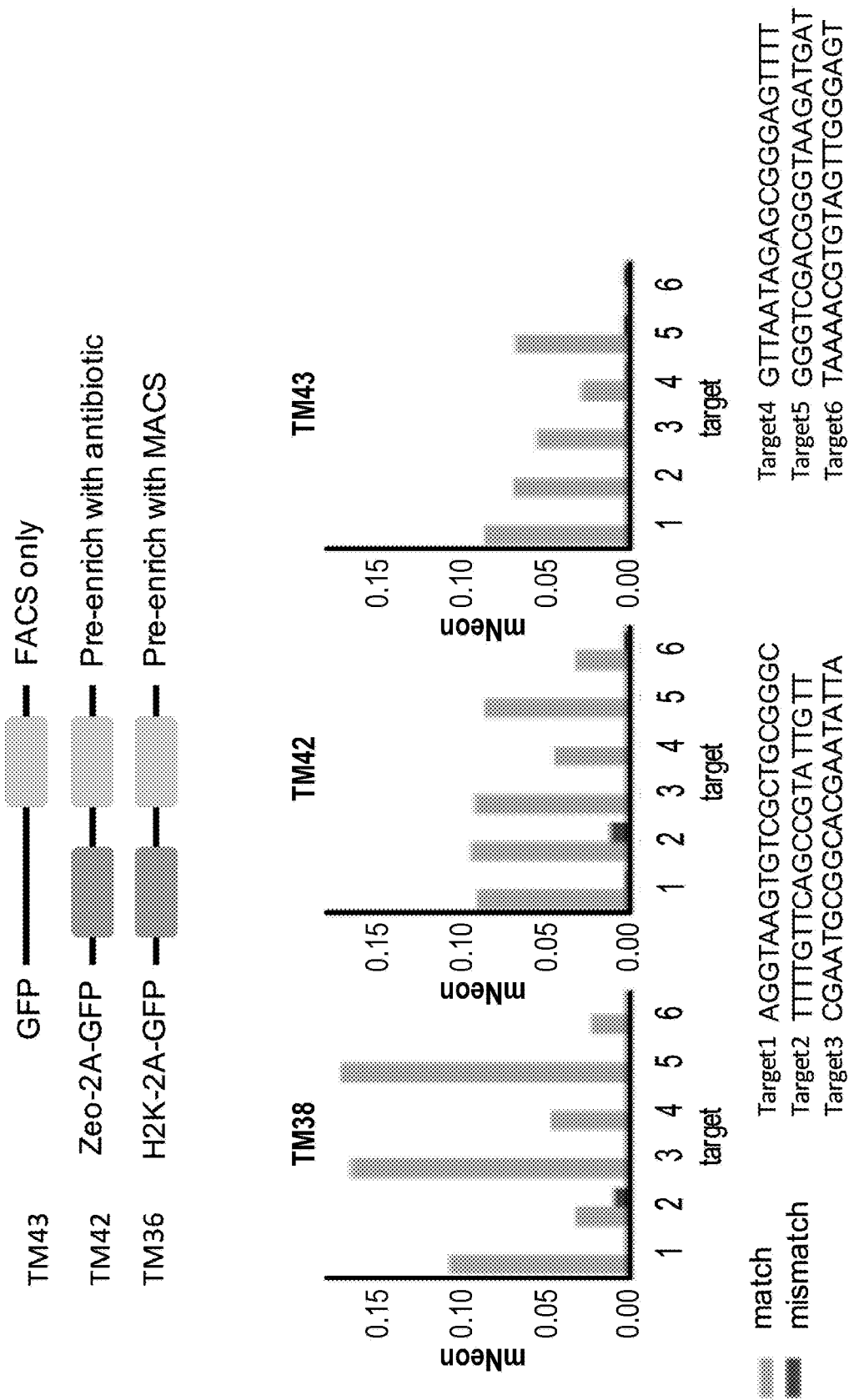
FIG. 31—Shows the specificity and sensitivity of retrieval vectors tested for multiple targeted barcodes (SEQ ID NO:34-39).
Figure 32:
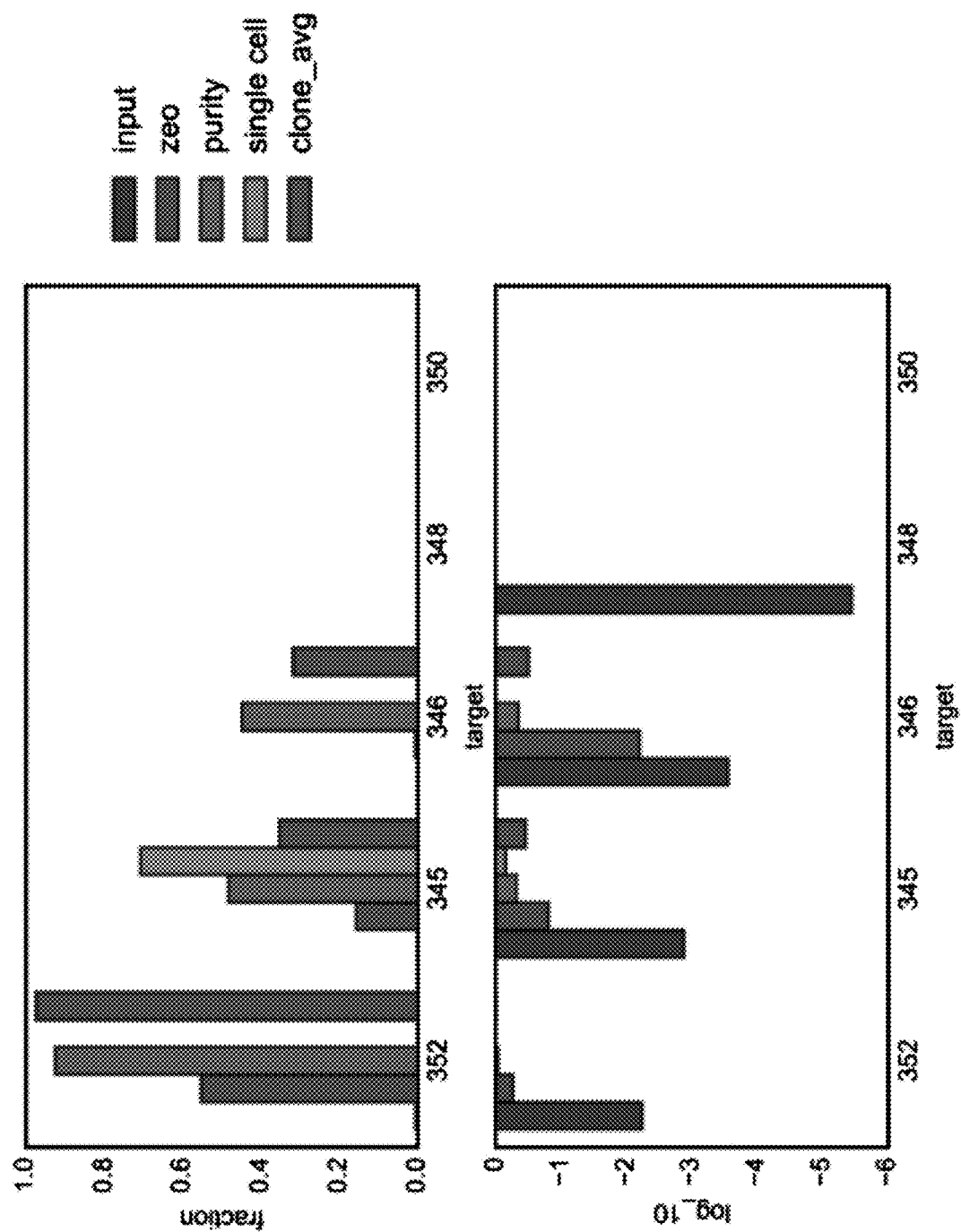
FIG. 32—Shows retrieval of hygro-resistant HeLa cells from a barcoded pool.

FIG. 29 illustrates the concepts of lineage tracing in a population of cells, retrieval of specific cells, and different barcode specific reporters that can be used for retrieval. The left panel shows a construct comprising a Pol III promoter driving expression of a non-targeting sgRNA. A library of non-targeting sgRNA constructs is transduced into a population of cells using a lentivirus library. The cells are treated plus and minus a selection (e.g., drug, perturbation). The barcodes are sequenced in the selected cells to identify barcodes that are enriched or depleted. The cells of interest can be retrieved from the original population of cells by introducing a barcode specific reporter to the cells. The barcode is specific for the sgRNA. If the cell has the sgRNA specific for the reporter then the reporter can be sorted or selected for (e.g., GFP). The guide sequence targets Cas9 to the barcode target, generating an Indel. In this construct if the frame is shifted +2, GFP is expressed and RFP is not expressed. If the frame is shifted +1, neither reporter is expressed. If the barcode is not targeted, RFP is expressed and GFP is not expressed. The reporter may be GFP, an antibody, a target protein, or a combination. Based on the reporter, cells can be enriched by FACS, pre-enriched with antibiotics, or pre-enriched with magnetic sorting (MACS). FIGS. 14 and 30 illustrate FACS sorting of selected cells. GFP positive cells are only detected with a matching guide sequence. FIG. 31 shows that retrieval vectors targeting six different sgRNA-barcodes were tested for activation by specific and non-specific sgRNA-barcodes in HeLa cells. Three vectors (TM36, TM42, TM43) containing alternate selection cassettes were assessed for GFP fluorescence. The vectors all showed high sensitivity and specificity in activating GFP. Pre-enrichment increased the sensitivity. The false positives using mismatched barcodes were very low to nonexistent. FIG. 32 illustrates retrieval from a mixed population of cells consisting of ~2% hygro-resistant and the remainder hygro-sensitive HeLa cells. The cells were barcoded and subjected to hygro selection and deep sequencing. Target retrieval vectors corresponding to hygro-resistant barcoded subpopulations were cloned and transduced into the original population prior to selection. The targeted subpopulations were enriched via FACS or zeocin selection. Cells containing the correct barcode were successfully retrieved for input rarity in the range 1%-0.01%. The input percentages for the hygro resistant cells targeted were less 1%. Retrieval was from a mix of HeLa cells where the drug-resistant cells were determined by barcode tracing and not spiked in pre-barcoded cells. Thus, the method allows retrieval from rarities in the range 1-0.01%.

Example 8—Methods

Library construction. Degenerate oligos for sgRNA-barcode library construction were synthesized by IDT and cloned into lentiGuide-Puro (Sanjana 2014) by Gibson assembly as in (JJ 2017). Approximately 300 ug of Gibson product was transformed into 25 uL of Endura electrocompetent cells (Lucigen). After a 1 hour recovery period, 0.1% of transformed bacteria were plated in a 10-fold dilution series on ampicillin plates to determine the number of successful transformants. The remainder of the transformed bacteria were cultured in 50 mL of LB with 50 ug/mL ampicillin for 16 hours at 30° C. Plasmid libraries were extracted using Plasmid MidiPlus kit (Qiagen) and sequenced to a depth of 95 million reads on Illumina Nextseq, corresponding to 13× coverage of 3.9 million barcodes. Lentivirus was prepared as in (JJ 2017) by transfecting a total of 10 million HEK 293FT cells. The library virus was determined by transduction and puromycin selection in HeLa-Tet-Cas9 cells to contain 600 million infective particles, corresponding to a 153× coverage of barcodes.

Barcoding of cell lines. HeLa-Tet-Cas9 cells were cultured in DMEM medium supplemented with 10% tetracycline-screened FBS (Hyclone) and 1% penicillin-streptomycin. sgRNA-barcodes were transduced as in (JJ 2017) and selected with 1 ug/mL puromycin for 5 days. The lentiviral multiplicity of infection was determined to be between 0.05 and 0.3 for all libraries, so that a majority of cells carry a single integrated sgRNA-barcode. Barcoded cell lines were expanded to a total of 10 million cells and cryopreserved in aliquots of 1 million cells for subsequent drug selection and retrieval.

PC9 cells were cultured in DMEM media supplemented with 10% FBS and 1% penicillin-streptomycin. D458 medulloblastoma cells were cultured in DMEM/F12 media supplemented with 10% FCS and 1% GPS (glutamate, pen-strep). 4 million cells were transduced with the sgRNA barcode library (wells of 4×10^6 cells with virus) by spin infection (2000 rpm, 120 minutes, 30° C). Cells were harvested the following day and selected with 1 ug/ml puromycin at 48 hours. Cells were counted (and compared to a no-puromycin treatment control) and the well that achieved a MOI of 30% was expanded for subsequent drug selection and retrieval experiments.

Drug resistance experiments—PC9 and Erlotinib. Barcoded PC9 (fingerprint verified) cells were treated with DMSO or Erlotinib at two concentrations (60 nM or 1 uM) in multiple replicate plates (5×DMSO and 5× each drug concentration). 4 million cells of barcoded PC9 cells were plated in each replicate plate in presence of DMSO or Erlotinib. Barcoded PC9 cells were also frozen in 10% DMSO/FCS for future retrievable. In addition, cells were also collected for DNA-extraction to determine barcode representation at the early-time point. Cells were retreated with compound every 3-4 days. For DMSO treated cells (or cells treated with 60 nM of Erlotinib), cells were counted, passaged or split every 3-4 days, maintaining a minimum representation of 4 million cells. Cells were cultured in DMSO or Erlotinib prior to harvesting for DNA extraction for barcode sequencing and deconvolution.

Drug resistance experiments—D458 and JQ1. Barcoded D458 medulloblastoma cells (fingerprint verified) cells were treated with DMSO or JQ1 (obtained from Drs Bradner and Qi) at a concentration of 2 uM in multiple replicate plates (5×DMSO and 5× each drug concentration). 4 million cells of barcoded D458 cells were plated in each replicate plate in presence of DMSO or JQ1. Barcoded JQ1 cells were also frozen in 10% DMSO/FCS for future retrievable. In addition, cells were also collected for DNA-extraction to determine barcode representation at the early-time point. Cells were retreated with compound every 3-4 days. Cells were counted, passaged or split every 3-4 days, maintaining a minimum representation of 4 million cells. Cells were cultured in DMSO or JQ1 for a total of xx days prior to harvesting for DNA extraction for barcode sequencing and deconvolution.

Drug resistance experiments—HeLa and hygromycin. HeLa cells were infected with a lentiviral ORF construct (xx vector cloned to express V5-LacZ) that harbors a hygromycin resistance cassette. After selection with hygromycin, HeLa-LACZ cells were spiked into uninfected cells at a 1:100 and 1:10,000 concentration. Cells were then infected with the Evoseq library at a low MOI. Following selection with puromycin, Applicants plated cells with differing cell numbers (to achieve a 'bottleneck' of the number of barcoded cells) and expanded them. Cells were frozen in liquid nitrogen in replicates of 1×10^6 cells. Replicates were thawed for barcoding experiments (1×ETP, xDMSO and x hygromycin at 400 ug/ml). Replicate cells were cultured in DMSO or hygromycin following which DNA was extracted from both the ETP control and DMSO/hygromycin treated replicates for barcode sequencing and deconvolution.

Library deconvolution. Genomic DNA was extracted and prepared for deep sequencing as in (JJ 2017). Libraries were sequenced to a minimum depth of 18 million reads, corresponding to a barcode coverage of >80×.

Retrieval with reporter construct. Oligos containing target sequences matching barcodes of interest were synthesized (IDT) and cloned into frameshift reporter plasmids by golden gate assembly. Lentivirus was prepared as in (JJ 2017) and transduced HeLa-Tet-Cas9 cells into at an MOI of <0.3. After 5 days of selection with 10 ug/mL blasticidin, 1 ug/mL doxycyclin was added to induce Cas9 expression. Cells were harvested for deep sequencing as in (JJ 2017). Fluorescent protein expression was measured on a Cytoflex flow cytometer. Populations were sorted on a Sony-SH800 FACS machine, and expanded for two weeks before deep sequencing.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of recovering selecting one or more cells from mixed populations of cells comprising:
   a) tagging individual cells in a mixed population of cells with a guide molecule construct encoding a guide sequence from a library of constructs encoding different guide sequences, each guide sequence encoding a unique barcode sequence, and each guide sequence configured to guide a CRISPR-Cas effector protein to a target loci of a polynucleotide reporter construct, the polynucleotide reporter construct comprising the target loci, a first type of one or more markers that are out-of-frame, and a second type of one or more markers that are in frame,
   wherein one guide molecule construct is integrated into the genome of each cell, whereby the guide molecule construct is passed to its progeny upon propagation of the mixed population of cells;
   b) expanding the mixed population of cells for one or more generations, wherein each cell and the progeny of each cell in the mixed population of cells have the same guide molecule construct;
   c) splitting the mixed population of cells into one or more test populations and recovery populations;
   d) exposing the test population of cells to one or more perturbations;
   e) determining cells of interest comprising barcodes of interest by sequencing the test population of cells and assessing a ratio of the different barcode sequence counts;
   f) recovering the cells of interest by introducing to the recovery population polynucleotide reporter constructs comprising target loci for the guide sequences comprising the barcodes of interest and a CRISPR-Cas effector protein, or inducing expression within the cells of a CRISPR-Cas effector protein, wherein the guide sequence expressed in cells having the barcodes of interest guides the CRISPR-Cas effector protein to the target loci of the polynucleotide reporter construct, and wherein the CRISPR-Cas effector protein makes a frame shift edit at the target loci that shifts the first type of markers in frame wherein the first type of one or more markers are expressed, and wherein the second type of one or more markers are shifted out-of-frame wherein the second type of markers are no longer expressed;
   g) retrieving the cells of interest that express the first type of one or more markers.

2. The method of claim 1, wherein the one or more perturbations comprise one or more genetic or RNA perturbations, one or more chemical perturbations, one or more physical perturbations, or a combination thereof.

3. The method of claim 2, wherein the one or more genetic or RNA perturbations comprise one or more gene knock-ins; one or more gene knock-outs, one or more nucleotide insertions, deletions, or substitutions; one or more transpositions; or one or more inversions.

4. The method of claim 2, wherein the one or more physical perturbations comprise different temperatures, pH, growth media conditions, atmospheric $CO_2$ concentrations, atmospheric $O_2$ concentrations, and/or sheer stresses.

5. The method of claim 2, wherein the one or more chemical perturbations comprise exposing a set of samples comprising the mixed population of cells to a different chemical compound or combination of chemical compounds, a different concentration of a same chemical compound or combination of chemical compounds, or different concentrations of different chemical compounds or combinations of chemical compounds.

6. The method of claim 5, wherein the chemical compound or combination of chemical compounds is a therapeutic agent or combination of therapeutic agents.

7. The method of claim 1, wherein the cells of interest are determined by identifying a phenotype of interest, optionally comprising changes in growth characteristics, morphology, motility, cell death, cell-to-cell contacts, antigen presentation and/or synapsing, and/or interactions with patterned substrates.

8. The method of claim 7, wherein the cells of interest are cells that are resistant to the one or more genetic or RNA perturbations, or to the one or more therapeutic agents or combinations of therapeutic agents.

9. The method of claim 1, wherein the cells are retrieved using fluorescence-activated cell sorting.

* * * * *

UNITED STATES PATENT AND TRADEMARK OFFICE
CERTIFICATE OF CORRECTION

PATENT NO. : 11,547,614 B2
APPLICATION NO. : 16/760906
DATED : January 10, 2023
INVENTOR(S) : Pratiti Bandopadhayay et al.

It is certified that error appears in the above-identified patent and that said Letters Patent is hereby corrected as shown below:

On the Title Page

On page 3, in Column 1, under "Other Publications", Line 21, delete "Anemai" and insert -- Anemia --.

On page 3, in Column 2, under "Other Publications", Line 15, delete "wiht" and insert -- with --.

On page 3, in Column 2, under "Other Publications", Line 31, delete "AIDSrelated" and insert -- AIDS related --.

On page 4, in Column 2, under "Other Publications", Line 68, delete ""MicroCorrespondence:" and insert -- "Micro Correspondence: --.

In the Specification

In Column 13, Line 29, delete "type" and insert -- type NNNNNNNNNNNN. --.

In Column 16, Line 12, delete "666-6′73," and insert -- 666-673, --.

In Column 21, Line 17, delete "(3-actin" and insert -- β-actin --.

In Column 21, Line 30, delete "Cash," and insert -- Cas6, --.

In Column 24, Line 57, delete "chemicially" and insert -- chemically --.

In Column 24, Line 58, delete "ethyl(cEt)." and insert -- ethyl (cEt). --.

In Column 25, Line 66, delete "fulfones," and insert -- sulfones, --.

In Column 29, Line 2, delete "02" and insert -- O2 --.

Signed and Sealed this
Fifteenth Day of August, 2023

Katherine Kelly Vidal
*Director of the United States Patent and Trademark Office*

CERTIFICATE OF CORRECTION (continued)
U.S. Pat. No. 11,547,614 B2

In Column 29, Line 46, delete "sigtrans; 4/164/r52)," and insert -- sigtrans;4/164/rs2), --.

In Column 32, Line 2, delete "al" and insert -- al. --.

In Column 35, Line 28, delete "Crystal" and insert -- "Crystal --.

In Column 35, Line 29, delete "2015)" and insert -- 2015). --.

In Column 40, Line 5, delete "US2014-" and insert -- US 2014- --.

In Column 45, Line 37, delete "TetRcas9-HeLa" and insert -- TetR-cas9-HeLa --.

In Column 47, Line 29, delete "MidiPlus" and insert -- Midi Plus --.

In the Claims

In Column 59, Line 26, in Claim 1, after "recovering" delete "selecting".

In Column 60, Line 26, in Claim 1, before "wherein" insert -- and --.